US011017332B2

(12) United States Patent
Nacey

(10) Patent No.: US 11,017,332 B2
(45) Date of Patent: *May 25, 2021

(54) APPARATUS AND METHOD FOR THE MOBILE VISUAL DISPLAY AND MODIFICATION OF BED MANAGEMENT INFORMATION AND PATIENT PLACEMENT INFORMATION

(71) Applicant: TeleTracking Technologies, Inc., Pittsburgh, PA (US)

(72) Inventor: Gene E. Nacey, Leechburg, PA (US)

(73) Assignee: TeleTracking Technologies, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/514,493

(22) Filed: Jul. 17, 2019

(65) Prior Publication Data
US 2020/0012976 A1 Jan. 9, 2020

Related U.S. Application Data

(63) Continuation of application No. 15/717,374, filed on Sep. 27, 2017, now Pat. No. 10,366,356, which is a continuation of application No. 11/221,418, filed on Sep. 7, 2005, now Pat. No. 9,779,366.

(60) Provisional application No. 60/608,049, filed on Sep. 7, 2004.

(51) Int. Cl.
*G06Q 10/06* (2012.01)
*G08B 5/22* (2006.01)

(52) U.S. Cl.
CPC ............ *G06Q 10/06* (2013.01); *G08B 5/221* (2013.01)

(58) Field of Classification Search
CPC ...... G06Q 10/02; G06Q 10/025; G06Q 10/06; G06Q 50/00; G06Q 50/22; G06Q 50/24; G06F 10/322; G06F 10/323; G06F 19/323; G06F 19/327; G08B 5/22
See application file for complete search history.

(56) References Cited

U.S. PATENT DOCUMENTS

| | | | | |
|---|---|---|---|---|
| 5,867,821 A | * | 2/1999 | Ballantyne | G06Q 10/10 705/2 |
| 2003/0074222 A1 | * | 4/2003 | Rosow | G06Q 10/0875 705/2 |
| 2008/0312975 A2 | * | 12/2008 | Rosow | G06Q 50/24 705/5 |

* cited by examiner

*Primary Examiner* — Van T Trieu
(74) *Attorney, Agent, or Firm* — Ference & Associates LLC

(57) ABSTRACT

An apparatus and method for using a mobile computer device for graphically displaying and modifying information in a manner to enhance comprehension of the information and allowing for the mobile and decentralized management of information to be accomplished, wherein such information may be related to bed management and patient placement information and, furthermore, enabling the information of interest to be organized, sorted, and used in various useful and novel ways.

20 Claims, 24 Drawing Sheets

| AssignedEdit 522301 M5B |
|---|
| Last Name: CLEVER |
| First Name: DORIS |
| ID#: 1475576 |
| Age: 27 |
| Sex: F |
| Diagnosis: Data Removed |
| Adm. Phy: BATTLE CONSTAN |
| Att. Phy: BATTLE CONSTAN |
| Comments: test |

[ CHANGE TO REQUEST ]  [ CANCEL ]

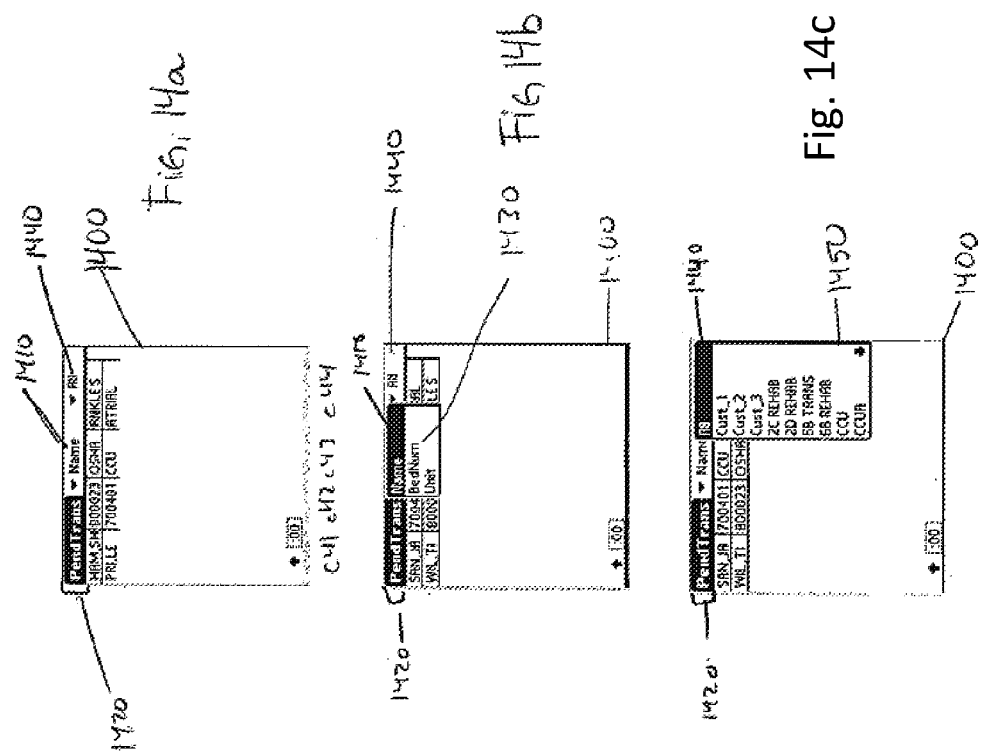

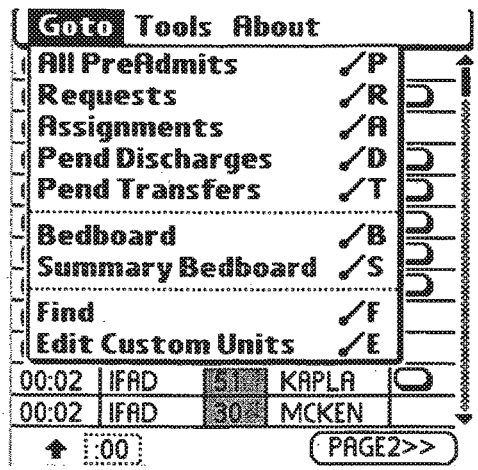

| Bedboard | ▼ Unit | | | ▼ All | | | |
|---|---|---|---|---|---|---|---|
| Unit | B | S | R | A | P | V | C |
| 2C REH | 18 | 18 | 2 | 2 | 1 | 2 | 15 |
| 2D REH | 44 | 44 | 0 | 2 | 1 | 4 | 39 |
| 5B TRA | 0 | 0 | 0 | 0 | 0 | 0 | 0 |
| 6B REH | 6 | 6 | 1 | 0 | 0 | 0 | 6 |
| CCU | 12 | 12 | 0 | 0 | 1 | 1 | 12 |
| CCUA | 6 | 6 | 1 | 0 | 0 | 0 | 6 |
| CPOA | 8 | 8 | 0 | 0 | 0 | 6 | 2 |
| CTSU | 12 | 10 | 0 | 0 | 0 | 1 | 9 |
| HCOA | 0 | 0 | 0 | 0 | 0 | 0 | 0 |
| HOLD | 0 | 0 | 0 | 1 | 0 | -1 | 0 |

APPARATUS AND METHOD FOR THE MOBILE VISUAL DISPLAY AND MODIFICATION OF BED MANAGEMENT INFORMATION AND PATIENT PLACEMENT INFORMATION

RELATED APPLICATIONS

This application is a continuation application of U.S. patent application Ser. No. 15/717,374 (U.S. Pat. No. 10,366,356), filed on Sep. 27, 2017, entitled "Apparatus and Method for the Mobile Visual Display and Modification of Bed Management Information and Patient Placement Information," which is a continuation application of U.S. patent application Ser. No. 11/221,418 (U.S. Pat. No. 9,779,366), filed Sep. 7, 2005, entitled "Apparatus and Method for the Mobile Visual Display and Modification of Bed Management Information and Patient Placement Information," which is a non-provisional application of U.S. Application Ser. No. 60/608,049 filed on Sep. 7, 2004, each of which is hereby incorporated by reference.

FIELD OF THE INVENTION

The present invention relates generally to a hospital capacity workflow management system, and more particularly to an apparatus and method for a mobile, decentralized approach to the efficient utilization of bed management and patient placement information.

BACKGROUND OF THE INVENTION

Nurses and other attending staff in a hospital ward or hospital wing work under conditions involving high pressure, stress and long hours. These care givers must remain alert to respond to patient needs, in both emergency and non-emergency situations. Due to economic practicalities and the ever-increasing costs of medical care, it is necessary to make the most efficient use of nurses and staff on call in a hospital ward or hospital wing, particularly at night when nurse and staff levels are maintained at a minimum. While technological and medical breakthroughs have led to amazing treatment advances over the past few decades, many other factors have led to challenges in the delivery of healthcare services. For example, the number of available hospital beds has drastically decreased during this same period as a result of the many hospital closings and consolidations occurring across the county. Unfortunately, the reduction in beds comes at a time when demand for them is increasing. The increase in demand stems from the rising need for healthcare services as a result of factors like population growth and the aging "baby boomer" demographic. These and other factors have meant that it is becoming increasingly difficult for hospitals to meet the demands placed upon, which is often most apparent in the backlogs that can be easily observed in almost every Emergency Department throughout the nation. Compounding the physical capacity issues are human capacity and process or workflow components as well. The shortage of clinical personnel, such as nurses and technologists, also impacts the ability of hospitals to deliver care in an efficient manner. Sadly, the current processes of handling bed management and patient placement in many hospitals today, leads to delays, lag time and bottlenecks in patient flow. Thus, there is presently a clear need for a more efficient process.

The desire, however, to optimize hospital efficiency is of secondary importance relative to the primary objective, that of providing a high level of medical care to patients. For example, if nurse and staff levels are reduced for the sake of efficiency without any corresponding simplification of duties and responsibilities, the level of patient care will decrease. Therefore, it is desirable to maximize the efficiency of nurses and staff on call in a hospital wing or hospital ward, but to do so in a manner which does not increase the work load or stress levels of these professional care givers nor decrease the level of patient care. Thus, it is of primary importance for hospitals to have the ability to access and manage information related to bed management and patient placement, including the existing demand for patients waiting for available beds, managing the discharge and transportation of patients, managing room preparation and cleaning for new patients, and the management of the placement of their patients without causing increased hardship and confusion to the hospital personnel.

One approach to maximizing the efficiency of nurses and other hospital staff involves providing information needed by these professionals in a location remote from a patient room. For instance, U.S. Pat. No. 5,699,038 to Ulrich et al. discloses a bed status information system of hospital beds which provides remote instantaneous retrieval of unique identification information about the bed and provides status information related to the position of the bed, the configuration of the mattress surface, the status of the safety systems on the bed, and the current state of various patient care systems integrated with the bed. Monitoring of patient information therefore does not require attendance within the room to locally view and interpret various types of information. U.S. Pat. No. 5,867,821 to Ballantyne et al. discloses a method and apparatus for electronically accessing and distributing personal health care information and services in hospitals and homes in which certain information, ranging from patient health record information to patient and operating room monitoring information, is distributed to a nursing station within a hospital.

Providing information to nurses and other hospital staff at a centralized remote location away from patient room creates certain problems however. Among the problems is presenting information to the medical professionals in a way that assists them in effectively monitoring the information without increasing their level of stress, which may occur if they feel overwhelmed by the amount of information provided and time required to retrieve it. Moreover, simply providing access to information and even the ability to manage or modify the information at one particular location can be futile in a busy hospital environment. This is due to the fact that many of the persons responsible for patent flow are often themselves in a state of movement about the hospital thereby preventing relevant information from being acted upon by the personnel having a need for the information or who have knowledge of updated information. A need for a solution to the aforementioned problems has therefore been recognized.

SUMMARY OF THE INVENTION

The present invention, in accordance with at least one presently preferred embodiment, utilizes the capabilities of a mobile computer device (hereinafter "mobile device" or "device") within a wireless network environment to graphically display selected information in a manner which conveys the information to nurses and other hospital staff in a form which aids in comprehension of the information and allows for the remote, mobile, and decentralized approach to bed and patient placement information management to be accomplished. The decentralized approach, therefore, delegates the assigning of beds to either a mobile patient placement nurse/coordinator or patient access management/administrative personnel. Since, these personnel are rarely stationary so as to allow them to benefit from an immobile workstation the present invention is of particular beneficial use.

Specifically, information is preferably conveyed via a wireless network connection to a mobile computer device providing a graphical matrix display of various information related broadly to hospital bed management and patient placement, such information providing a timely reflection as to actual physical criteria within a hospital. A plurality of graphical matrices each containing information related broadly to bed management and patient placement can be maintained within a mobile device and displayed through a plurality of screens accessible to a user by selecting representative icons from a menu capable of being displayed on a mobile device. Additional information may be displayed by selecting an icon within the matrix. Through the use of various menus available to the user of a mobile device the information related broadly to bed management and patient placement can be manipulated in various ways so as to allow for, inter alia, the reorganizing and sorting of information, as well as updating information to reflect actual changes occurring within the hospital itself.

Consequently, the present invention broadly contemplates a method and apparatus whereby hospital bed management information and patient placement information is modified, managed, and visually displayed to at least one mobile device user, thereby aiding nurses and other hospital placement staff in efficiently using such information.

In one aspect, the present invention provides an apparatus for modifying and graphically displaying bed management and patient placement information, the apparatus comprising: a display; an arrangement for producing a plurality of cells for being viewed on the display, the cells having a plurality of modifiable attributes; and a controller which modifies at least one of the attributes of at least one of the cells to convey information.

In another aspect the present invention provides an apparatus for modifying and graphically displaying bed management and patient placement information, the apparatus comprising: a display, an arrangement for producing a plurality of cells for being viewed on the display, the cells having a plurality of modifiable attributes, and a controller which modifies at least one of the attributes of at least one of the cells to convey information related to bed management and patient placement.

In another aspect, the present invention provides an apparatus for modifying and graphically displaying bed management and patient placement information, the apparatus comprising: a display and an arrangement for producing a plurality of icons for being viewed on the display, the icons conveying information related to bed management and patient placement.

In another aspect, the present invention provides an apparatus for modifying and graphically displaying bed management and patient placement information, the apparatus comprising: a display, an arrangement for producing a plurality of icons for being viewed on the display, the icons having a plurality of modifiable attributes, and a controller which modifies at least one of the attributes of at least one icon to convey information related to bed management and patient placement.

In another aspect, the present invention provides a method of modifying and graphically displaying bed management and patient placement information, the method comprising the steps of: displaying a plurality of cells, the cells having a plurality of modifiable attributes; and wherein at least one of the attributes of at least one of the cells is modified to convey information related to bed management and patient placement.

In another aspect, the present invention provides a method of modifying and graphically displaying bed management and patient placement information, the method comprising the steps of: displaying information related to at least one hospital patient, displaying at least one icon within said display of information related to at least one hospital patient, each icon corresponding to a plurality of modifiable attributes, and modifying the attributes of the icon to convey information about the patient.

In another aspect, the present invention provides a method of modifying and graphically displaying bed management and patient placement information, the method comprising the steps of: displaying information related to at least one hospital bed, displaying at least one icon within said information related to at least one hospital bed, each icon corresponding to a plurality of modifiable attributes, and modifying the attributes of the icon to convey information about the hospital bed.

In another aspect, the present invention provides a method of modifying and graphically displaying bed management and patient placement information, the method comprising the steps of: displaying a plurality of icons, displaying information related to at least one hospital patient, displaying at least one icon within said display of information related to at least one hospital patient, each icon corresponding to a plurality of modifiable attributes, modifying the attributes of the icon to convey information about the patient, displaying information related to at least one hospital bed, displaying at least one icon within said information related to at least one hospital bed, each icon corresponding to a plurality of modifiable attributes, and modifying the attributes of the icon to convey information about the hospital bed.

In an additional aspect, the present invention provides a program storage device readable by machine, tangibly embodying a program of instructions executable by the machine to perform method steps for the visual presentation and user modification of information related to bed management and patient placement information, the method comprising the steps of: displaying a matrix; displaying a plurality of cells within said matrix; displaying a plurality of icons within said plurality of cells; displaying at least one bed icon corresponding to information related to at least one hospital bed and having modifiable attributes; modifying the attributes of said bed icon to convey information about the hospital bed; displaying at least one patient icon corresponding to information related patient placement and having modifiable attributes; and modifying the attributes of said patient icon to convey information about said patient placement.

In an additional aspect, the present invention provides a program storage device readable by machine, tangibly embodying a program of instructions executable by the machine to perform method steps for the visual presentation and user modification of information about the bed management and patient placement information, the method comprising the steps of: displaying a matrix, displaying at least one cell within the matrix, each cell corresponding to information related to at least one modifiable attribute, and having a plurality of modifiable attributes, and modifying the attributes of the cell to convey information.

In an additional aspect, the present invention provides a program storage device readable by machine, tangibly embodying a program of instructions executable by the machine to perform method steps for the visual presentation and user modification of information about the bed management and patient placement information, the method comprising the steps of: displaying a matrix, displaying a plurality of cells within the matrix, at least one bed cell corresponding to information related to at least one hospital bed and having modifiable attributes, and modifying the attributes of said bed cell to convey information about the hospital bed; at least one patient cell within the matrix corresponding to information related to patient placement and having modifiable attributes, and modifying the attributes of said patient cell to convey information about said patient placement.

For a better understanding of the present invention, together with other and further features and advantages thereof, reference is made to the following description, taken in conjunction with the accompanying drawings, and the scope of the invention will be pointed out in the appended claims.

BRIEF DESCRIPTION OF THE DRAWINGS

FIG. 3a illustrates a graphical depiction of the first page of a "Requests Screen" display in accordance with an embodiment of the present invention;

FIG. 3b illustrates a graphical depiction of the second page of a "Requests Screen" display in accordance with an embodiment of the present invention;

FIG. 4a illustrates a graphical depiction of a sorting options window in a "Requests Screen" display of a mobile device in accordance with an embodiment of the present invention;

FIG. 4b illustrates a graphical depiction of a patient units selection display of a mobile device in accordance with an embodiment of the present invention;

FIG. 7a illustrates a graphical depiction of a "Request Edit Screen" display of a mobile device in accordance with an embodiment of the present invention;

FIG. 7b illustrates a graphical depiction of a Request Edit Screen Unit Icon drop-down menu display of a mobile device in accordance with an embodiment of the present invention;

FIG. 7c illustrates a graphical depiction of a Bed Identification Number Menu display of a mobile device in accordance with an embodiment of the present invention;

FIG. 7d illustrates a graphical depiction of an "Assignment Confirmation Window" display of a mobile device in accordance with an embodiment of the present invention;

FIG. 8a illustrates a graphical depiction of the first page of an "All PreAdmits Screen" display of a mobile device in accordance with an embodiment of the present invention;

FIG. 8b illustrates a graphical depiction of the second page of an "All PreAdmits Screen" display of a mobile device in accordance with an embodiment of the present invention;

FIG. 9a illustrates a graphical depiction of a sorting options window in an "All PreAdmits Screen" display of a mobile device in accordance with an embodiment of the present invention;

FIG. 9b illustrates a graphical depiction of a dropdown Patient Units selection window in an "All PreAdmits Screen" display of a mobile device in accordance with an embodiment of the present invention;

FIG. 10 illustrates a graphical depiction of a change-to-request window display of a mobile device in accordance with an embodiment of the present invention;

FIG. 11a illustrates a graphical depiction of the first page of an "Assigned Screen" window display of a mobile device in accordance with an embodiment of the present invention;

FIG. 11b illustrates a graphical depiction of the second page of an "Assigned Screen" window display of a mobile device in accordance with an embodiment of the present invention;

FIG. 12a illustrates a graphical depiction of a sorting options window in an "Assigned Screen" display of a mobile device in accordance with an embodiment of the present invention;

FIG. 12b illustrates a graphical depiction of a dropdown Patient Units selection window in an "Assigned Screen" display of a mobile device in accordance with an embodiment of the present invention;

FIG. 14a illustrates a graphical depiction of a "Pending Transfers Screen" display of a mobile device in accordance with an embodiment of the present invention;

FIG. 14b illustrates a graphical depiction of a sorting options window in an "Pending Transfers Screen" display of a mobile device in accordance with an embodiment of the present invention;

FIG. 14c illustrates a graphical depiction of a dropdown Patient Units selection display of a mobile device in accordance with an embodiment of the present invention;

FIG. 15a illustrates a graphical depiction of a dropdown "Goto" selection display of a mobile device in accordance with an embodiment of the present invention;

FIG. 15b illustrates a graphical depiction of a "Bedboard Screen" window display of a mobile device in accordance with an embodiment of the present invention;

FIG. 18 illustrates a graphical depiction of an Electronic Bedboard Sorting Options Screen display of a mobile device in accordance with an embodiment of the present invention;

FIG. 19 illustrates a graphical depiction of an Electronic Bedboard Sorting Options Screen "Show Icon" pop-up window display of a mobile device in accordance with an embodiment of the present invention;

FIG. 19a illustrates a graphical depiction of a dropdown Patient Units selection display of a mobile device in accordance with an embodiment of the present invention;

FIG. 20 illustrates a graphical depiction of a "Summary Bedboard Screen" display of a mobile device in accordance with an embodiment of the present invention;

FIG. 21 illustrates a graphical depiction of a sorting options window in an "Summary Bedboard Screen" display of a mobile device in accordance with an embodiment of the present invention;

FIG. 22 illustrates a graphical depiction of a dropdown "Patient Units" selection display of a mobile device in accordance with an embodiment of the present invention;

DETAILED DESCRIPTION OF THE PREFERRED EMBODIMENTS

While the Detailed Description of the Preferred Embodiments describe the implementation of the invention on a device running the Palm Operating System (OS), e.g. a Palm Pilot, it should be understood that the present invention may be implemented on any suitable mobile device, including those devices operating WindowsCE and Pocket PC. Therefore, it should be understood the present embodiment may provide for display nomenclature, including icon names, that may differ between various devices. For example a Save Icon on one device may be a Done Icon on another device. By way of further example, a pull-up menu in one device could be implemented using a pull-down menu in another device. Likewise, a user's navigational flow for performing desired functions on one device may vary as compared to the navigational flow used on another device in carrying out the same functions. It should be further understood that the mobile device of the present invention is one having a controller allowing a user to interact and control the device, as well as input information into the device, which may take various forms.

Figure 1:
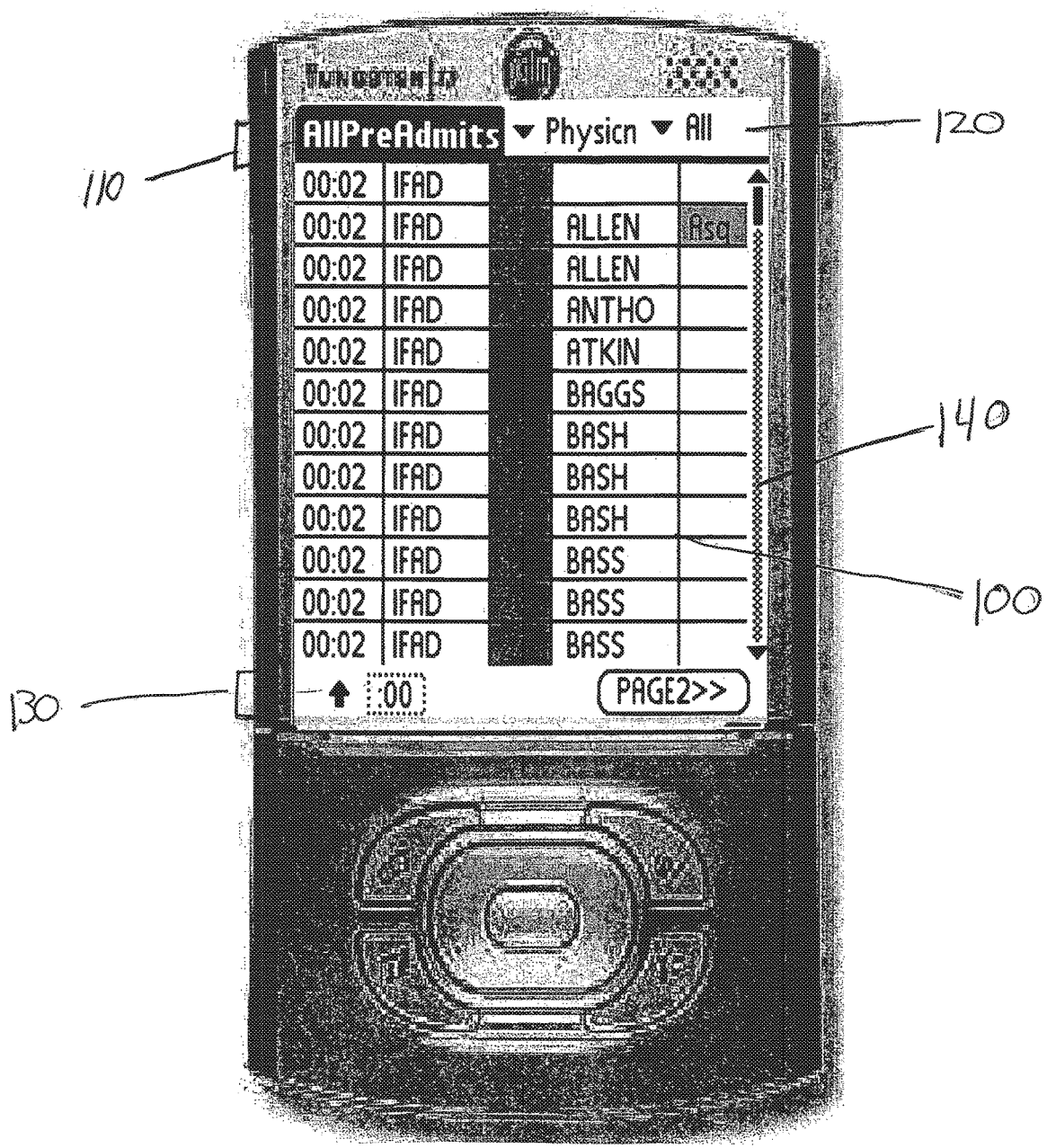
FIG. 1 illustrates a graphical depiction of a mobile computer device in accord with the at least one embodiment of the present invention and the general features of the mobile device's display screen.

As shown in FIG. 1, the general features of at least one preferred embodiment are provided, in which a Data Area 100 is displayed having a matrix forming cells containing various informational icons related to patient information. The Screen Title Menu 110 displays information regarding which screen is currently being displayed by the application, as well as providing a method for bringing up the various menus displayable for that screen. When a user selects any of the options displayed at the Screen Title Menu 110, drop-down menus are caused to be displayed through which a user can navigate to and from different screens. A Sort/Navigate function 120 allows for the sorting of current data and/or navigating within the application. A Bottom Screen Menu 130 includes functions available for the data displayed, e.g., sort in ascending/descending order, Refresh, Goto page 2, etc. . . . . . In the present embodiment, a scroll bar 140 allows a user to scroll the displayed information up or down. Various screens providing a user with numerous functions are capable of display upon a mobile device; the screens and corresponding functions associated with at least one presently preferred embodiment will now be addressed.

Figure 2:
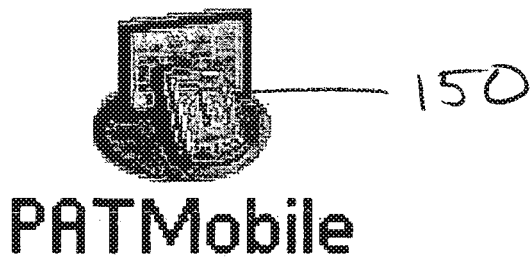
FIG. 2 illustrates a graphical "Start-Up Icon" in accordance with an embodiment of the present invention.
Figure 2A:
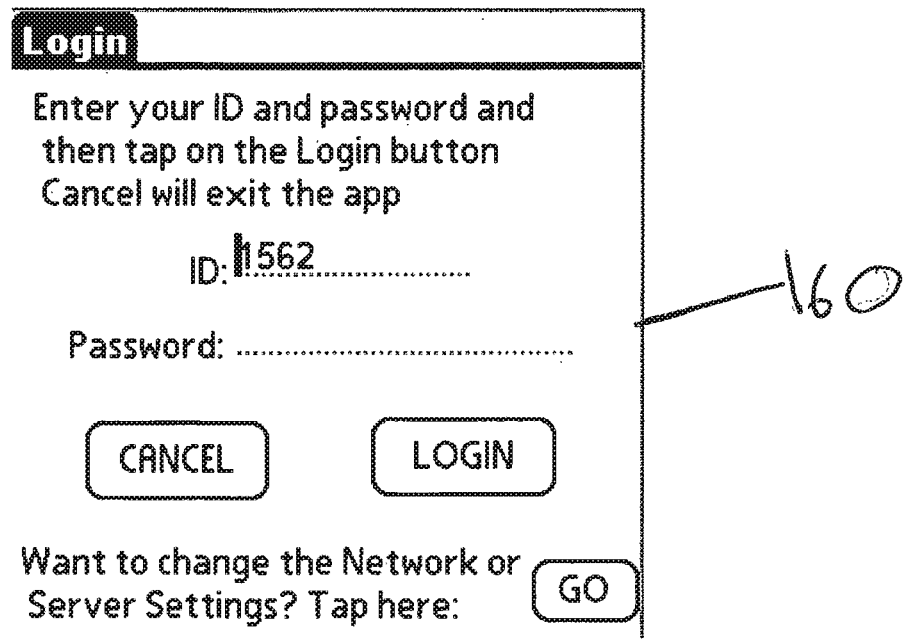
FIG. 2a illustrates a graphical depiction of a "Login Screen" display in accordance with an embodiment of the present invention
Figures 3A, 3B:
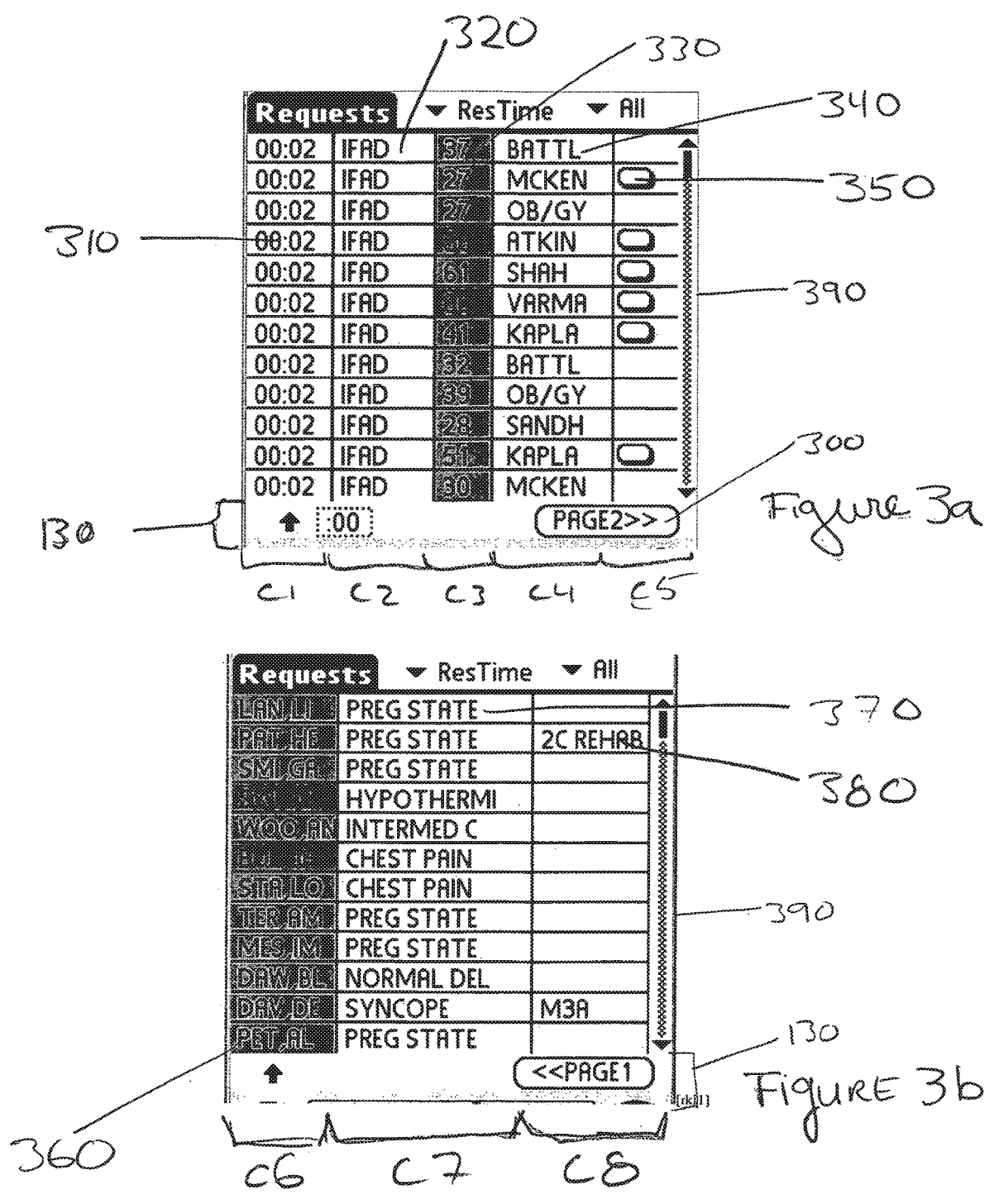

As shown in FIG. 2, at the mobile device's main screen a user will select a Start-Up Icon 150, thus, activating a Log-In Screen 160 requiring entry of user associated information before access is provided to the user. As shown in FIGS. 3a and 3b, the Requests Screen 390 is displayed. In the present preferred embodiment, the Requests Screen 390 consists of 8 columns displayed on two pages. A user can move between the two pages by selecting the Select Page Icon 300 displayed in the Bottom Screen Menu 130. A matrix having at least one graphically displayed icon provides information related to bed management and/or patient placement. To provide an example of the scope of the information which is displayed at the Request Screen 390, the informational columns of the Requests Screen 390 will be generally discussed, but first examples of the types of icons contained within the matrix's cells are given. The icon at reference numeral 310 depicts the time at which a particular request was made; the icon at reference numeral 320 depicts the department from which a particular request was made; the icon at reference numeral 330 depicts a patient's age; the icon at reference numeral 340 depicts a physician's name; the icon at reference numeral 350 depicts a notification that comments have been added to a particular patient's data and are accessible via selection of the icon; the icon at reference numeral 360 depicts a patient's abbreviated name; the icon at reference numeral 370 depicts an abbreviated version of a patient's diagnosis; and the icon at reference numeral 380 depicts a particular patient unit. Having discussed some of the types of icons capable of display within the matrix's cells, the information associated with the columns of the matrix will be discussed relating to at least one preferred embodiment of the invention.

As shown in FIG. 3a, the first page of the Requests Screen 390 contains 5 columns of information and, as shown in FIG. 3b, the second page of the Requests Screen contains 3 columns of information. For purposes of illustration, these columns are referenced, from left to right, as c1-c8. The first column, c1, contains information related to the Request Time, i.e., the time at which patients enter into the hospital's Admit-Discharge-Transfer (ADT) system or the time of a bed request. The second column, c2, provides information as to the Requester Department, i.e. the department of the hospital for which a bed request is made. The third column, c3, provides information of patients' ages. The fourth column, c4, provides information of patients' physician's names, which in the preferred embodiment are the admitting physician names or department names, unless attending physician names is selected via an Options Screen. The fifth column, c5, provides information related to patients' bed assignment statuses; the sixth column, c6, contains information of the patients' abbreviated names. The seventh column, c7, contains information of patients' abbreviated diagnoses. The eighth column, c8, contains information of patients' patient units. Before describing the other screens capable of being displayed upon the mobile device, some of the capabilities provided to the user related to the Requests Screen 390 of the present preferred embodiment will be discussed.

Figures 4A, 4B:
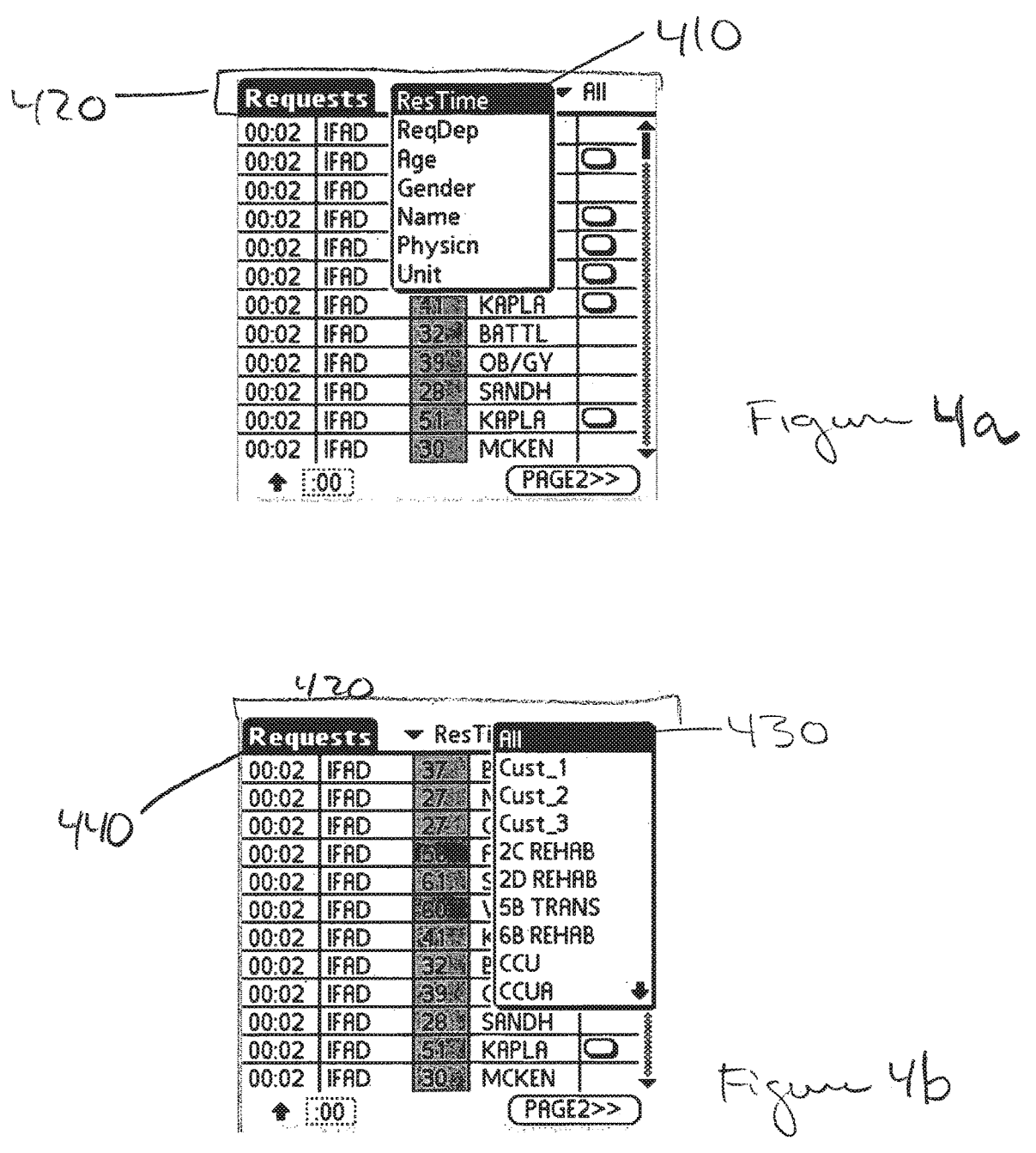

From the Requests Screen 390 the user can perform a variety of useful functions including: sorting information options; viewing additional information related to one or more patient units; viewing additional information related to user customized patient units; and assigning patient beds. The manner by which each of these functions is accomplished in the preferred embodiment will now be discussed in more detail. As shown in FIG. 4*a*, patient data represented at the Requests Screen 390 can be sorted in several user-selectable ways. By way of example, a user engaging the ResTime Tab 410 located in the middle of the Requests Screen Toolbar 420 will be provided a drop-down menu containing various sorting options for the user to choose from; which, in the present embodiment, include data sorted by Request Time; Requesting Department; Patient Age; Patient Gender; Patient Name; Physician; and Patient Unit.

Figure 5:
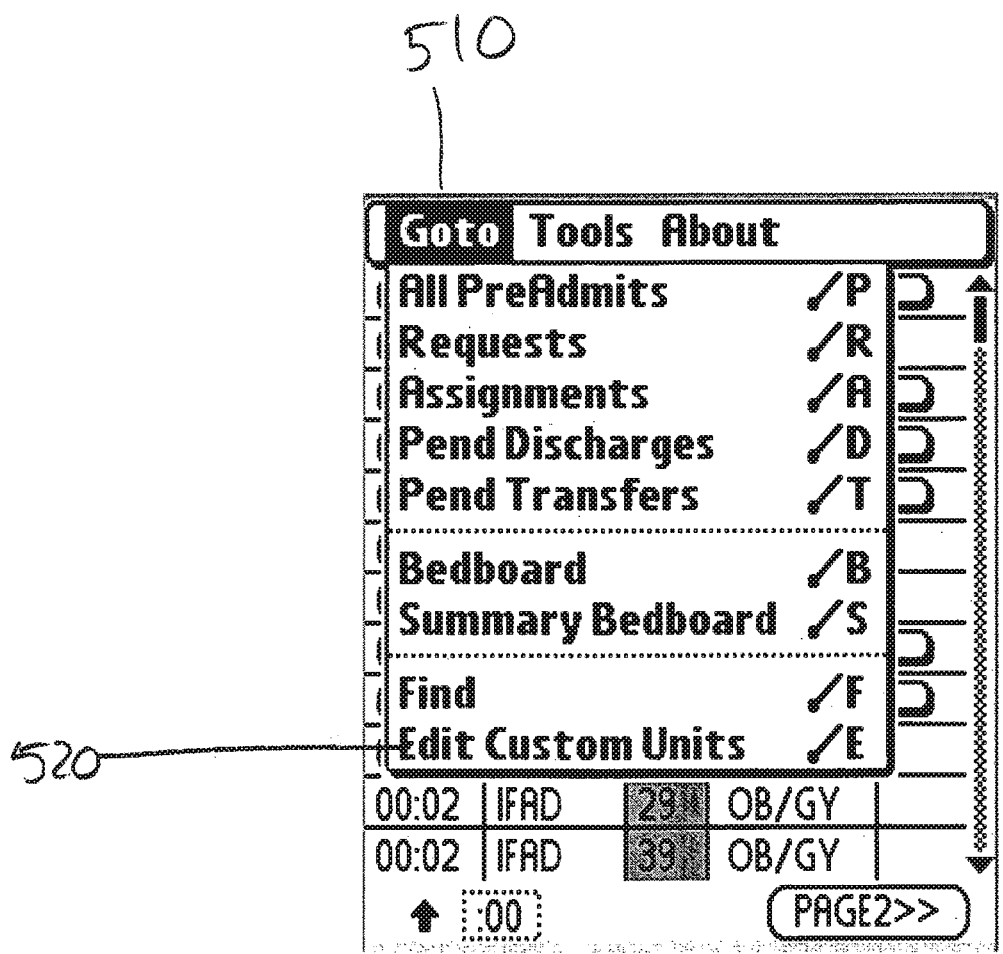
FIG. 5 illustrates a graphical depiction of a "Edit Custom Units" drop-down menu window display of a mobile device in accordance with an embodiment of the present invention.
Figure 6A:
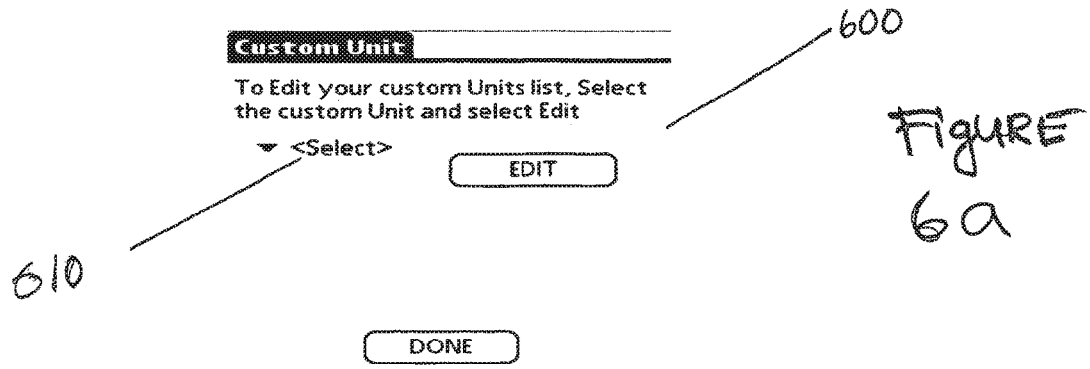
FIG. 6a illustrates a graphical depiction of a "Custom Unit Screen" display of a mobile device in accordance with an embodiment of the present invention.
Figure 6B:
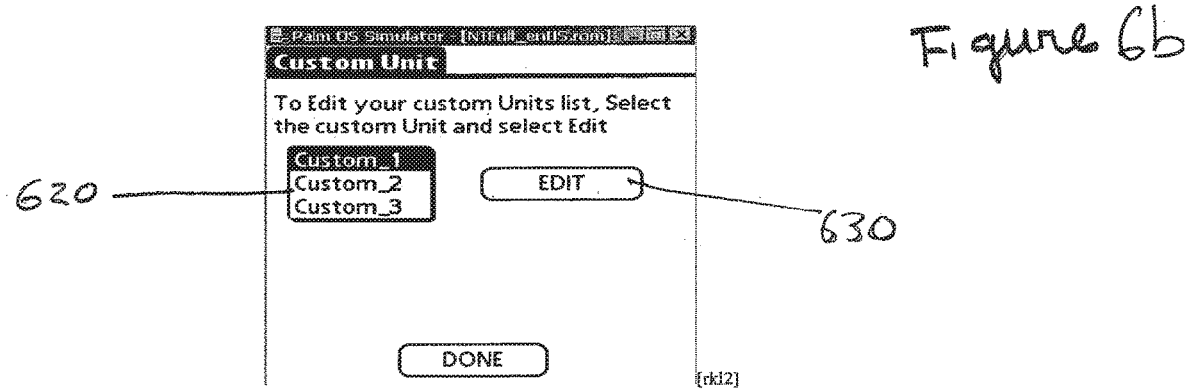
FIG. 6b illustrates a graphical depiction of a Custom Unit Screen select icon drop-down menu display of a mobile device in accordance with an embodiment of the present invention.
Figure 6C:
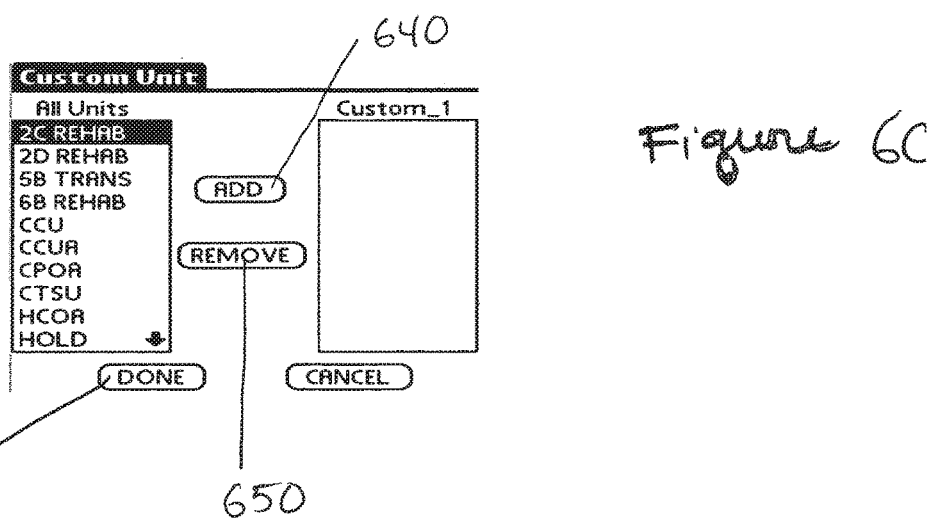
FIG. 6c illustrates a graphical depiction of a "Custom Unit Screen" add/remove display of a mobile device in accordance with an embodiment of the present invention.

As shown in FIG. 4*b*, users can also select to view information related to one or more specific patient units. By way of example, by selecting the All Tab 430 on the Requests Screen Toolbar 420 a drop-down menu from which the user can select a particular patient unit is displayed. In this example, the drop-down menu contains several specific patient units, as well as three customized patient unit groups from which the user can select. As shown in FIG. 5, customized patient units can be configured and edited by a user simply by selecting the Screen Identification Tab which, in this example, is also the Requests Tab 440. Selecting the Screen Identification Tab causes a Goto Drop-down Menu 510 to be displayed from which a user can navigate to any of the screens available for display upon the mobile device. In this instance, for example, while at the Requests Screen 390, upon selection of the Requests Screen Tab 440 a drop-down menu as shown in FIG. 5 is displayed, from which the user can select Edit Custom Units 520 upon which the Custom Unit Screen 600 is displayed as shown in FIG. 6*a*. The user's selection of the Select Icon 610 initiates a Custom Unit Drop-down Menu 620, thus, displaying the custom units available as shown in FIG. 6*b*. After selecting a particular custom unit, an Edit Icon 630 can be used to access a display of all the patient units that can be added to the particular custom unit selected using the Add Icon 640, as shown in FIG. 6*c*. Once added to the particular custom unit, a selected unit can be removed using the Remove Icon 650. Once satisfied, the user finishes the process using the Done Tab 660, thereby saving the customized unit created by the user. The general procedure for configuring and editing customized patient units is virtually identical for every screen of the mobile device in the present embodiment. It should, therefore, be noted that when this capability is referred to in relation to the other screens of the device, below, the detailed explanation above is applicable and is not cumulatively set forth.

It should also be observed that in the presently preferred embodiment shortcuts are available to the user for movement between various screens and functions, as shown by the shortcut icons in FIG. 5 for each of the device's screens. For example, tapping the device's stroke key followed by the letter "R" will cause the Requests Screen 390 to be displayed. (Note: other devices may not have shortcut capabilities, e.g. Pocket PC).

Figures 7A, 7B, 7C, 7D:
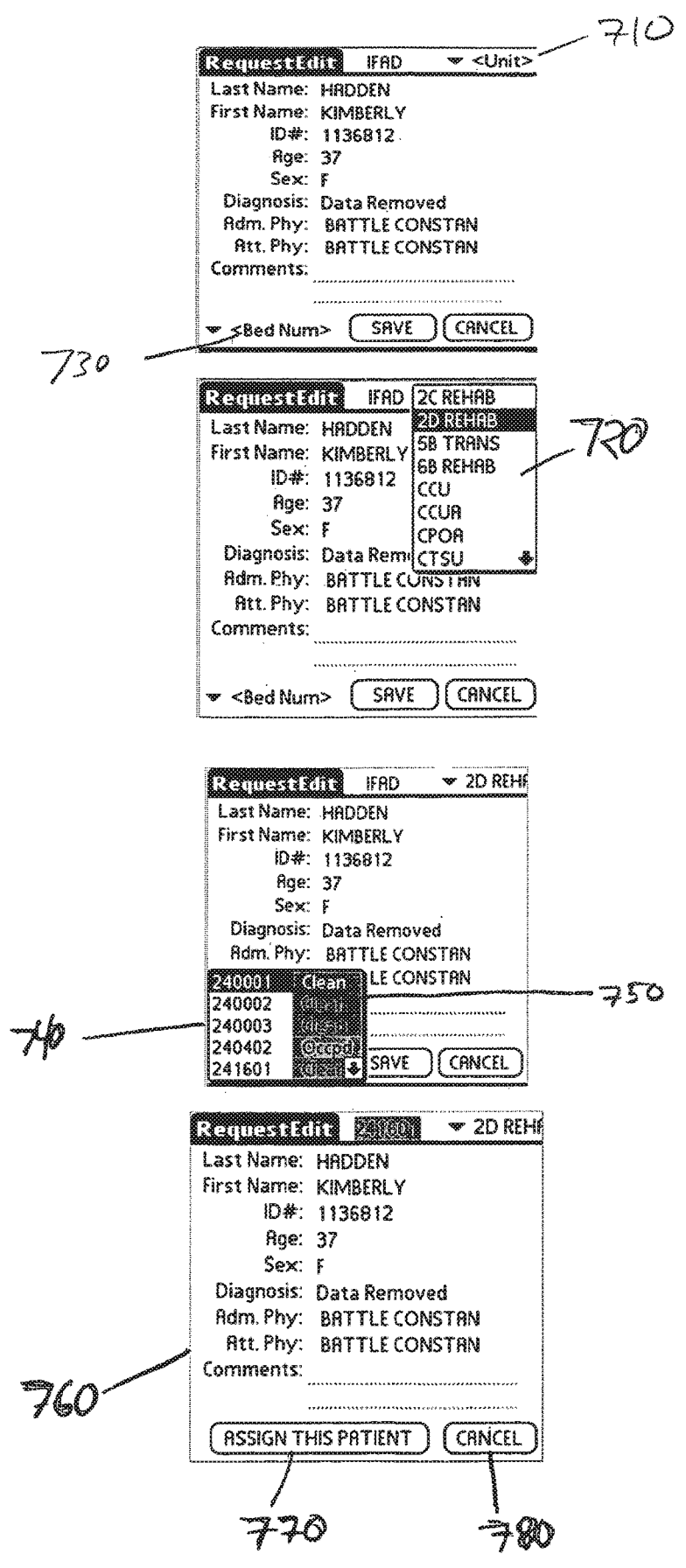

One of the many important functions of the presently embodied invention is the mobile device's capability to provide the user with the ability to assign patients beds from the device while moving about the hospital, thus, enabling efficient decentralized bed management and patient placement capabilities. By way of example, a user can focus upon the information contained in any of the first four columns related to a patient of interest thereby generating the display as shown in FIG. 7*a*. By selecting the Unit Icon 710 the user can focus data by selecting a particular patient unit from the Patient Units Menu 720. Upon selecting a particular patient unit from the Patient Units Menu 720, in this example 2D REHAB is selected, the user can focus the data by selecting the Bed Number Icon 730, which then provides a Bed Identification Number Menu 740, as shown in FIG. 7*c*, from which the user can select a particular bed of interest. In this embodiment the menu displayed upon selection of the Bed Number Icon 730 also provides the user with bed status information represented by the Bed Status Icons 750. After a bed is selected by the user an assignment confirmation window 760 is displayed wherein a user is provided the ability to assign the selected bed via the Assign Patient Icon 770. The user could also cancel the assignment using the Cancel Icon 780. Upon assignment the information is updated and stored by the mobile device. At particular intervals, as discussed below, a mobile device will transmit updated information to the network, thus, providing updated information to any devices accessing the network. In this embodiment the mobile device's connection is to a wireless network connectable to a plurality of other mobile devices having at least one wireless server capable of storing and transmitting the updated information received to and from any of a plurality of devices connected to the network. A wireless network, as well as various versions thereof, is well known in the art such that no further explanation need be presented at this time. Upon assignment all users of the system will have essentially instantaneous access to the current bed management and patient placement information, thus, increasing efficiency and avoiding needless over assignments.

Another screen available to the user via the mobile device's display in the present preferred embodiment is the All PreAdmits Screen 800 as shown in FIG. 8. This display is similar to that of the Requests Screen 390 discussed above. The All PreAdmits Screen 800 is a matrix display including 9 columns displayed on two pages. A user can move between the two pages by selecting the Select Page Icon 810 displayed in the Bottom Screen Menu 820. A matrix containing graphically displayed icons provides information to a user related to patients. To provide an example of the scope of information which is displayed in the All PreAdmits Screen 800 the columns included therein will be examined, but first examples of the types of icons contained within the matrix will be discussed.

The icon at reference numeral 830 depicts a time at which a request was made; the icon at reference numeral 840 depicts the department from which a request was made; the icon at reference numeral 850 depicts a patient's age; the icon at reference numeral 860 depicts a physician's name; the icon at reference numeral 870 depicts a bed's assignment information; the icon at reference numeral 880 depicts an abbreviated form of a patient's name; the icon at reference numeral 890 depicts a bed identification number; the icon at reference numeral 900 depicts a bed's status; and the icon at reference 910 depicts an abbreviated version of a patient's diagnosis. Having discussed some types of icons capable of display within the matrix in the preferred embodiment, the information associated with each of the columns will now be set forth.

Figures 8A, 8B:
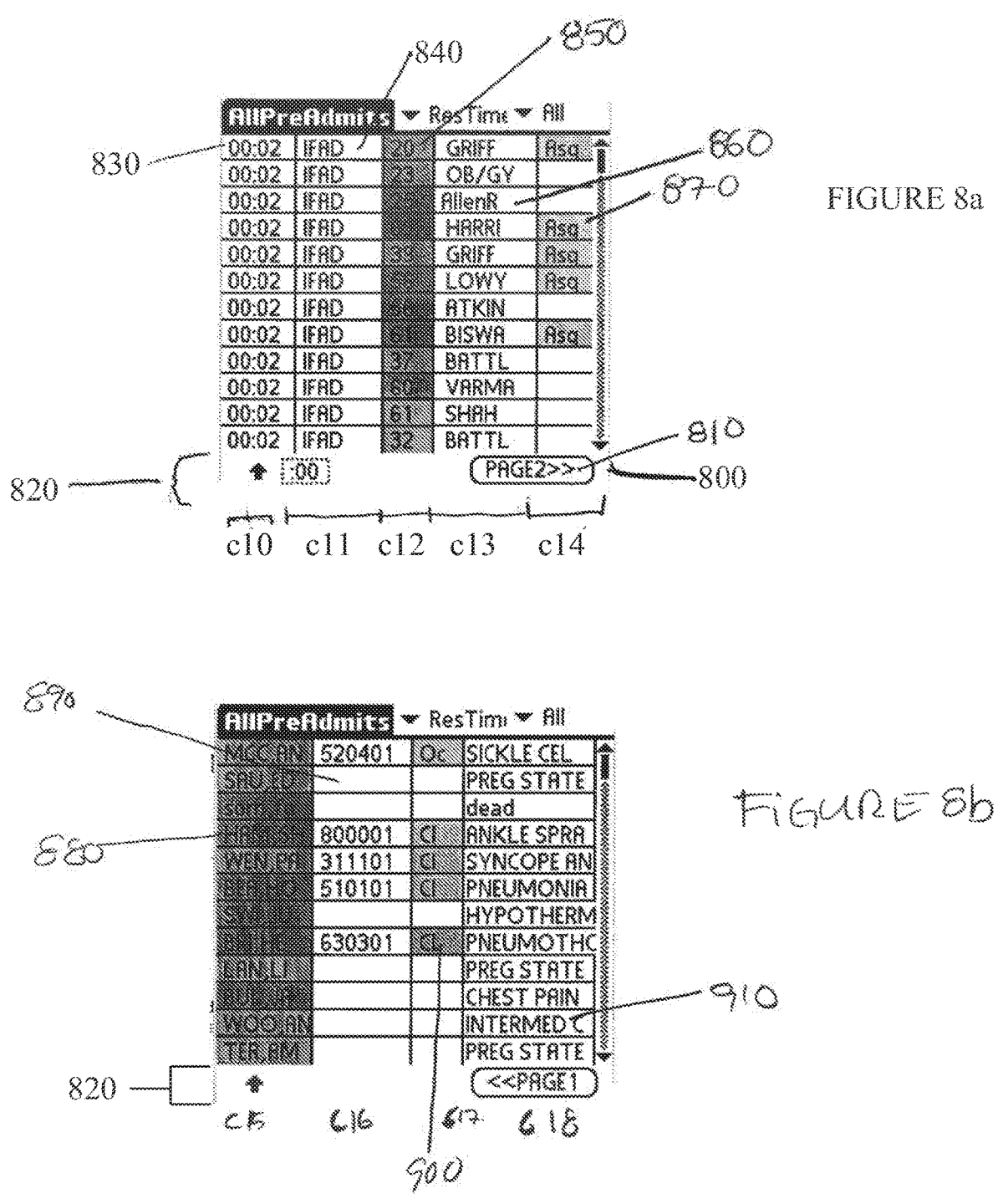

As shown in FIG. 8a, "page 1" of the All PreAdmits Screen contains 5 columns of information and, as shown in FIG. 8b, "page 2" of the All PreAdmits Screen contains 4 columns of information. These columns are referred to, from left to right, as c10-c19, respectfully. The first column, c10, contains information related to the Request Time; the second column, c11, provides information as to the Requester Department; the third column, c12, provides patients' ages; the fourth column, c13, provides patients' physician's names; the fifth column, c14, provides information of the bed assignment statuses; the sixth column, c15, contains information of patients' abbreviated names; the seventh column, c16, contains bed identification numbers; the eighth column, c17, contains information of beds' statuses, which can be in this preferred embodiment clean, dirty, occupied, in progress, or blocked; and the ninth column, c18, contains abbreviated patients' diagnoses.

Before turning to the other screens capable of being displayed upon the mobile device, some of the capabilities provided to the user related to the All Preadmits Screen 800 of the present preferred embodiment will be discussed. From the All Preadmits Screen 800 the user is provided a variety of useful functions including: sorting information options; viewing more information related to one or more patient units; viewing more information related to user customized patient units; and the ability to change assigned beds to bed requests. The manner in which each of these processes is accomplished will now be discussed in greater detail.

Figures 9A, 9B:
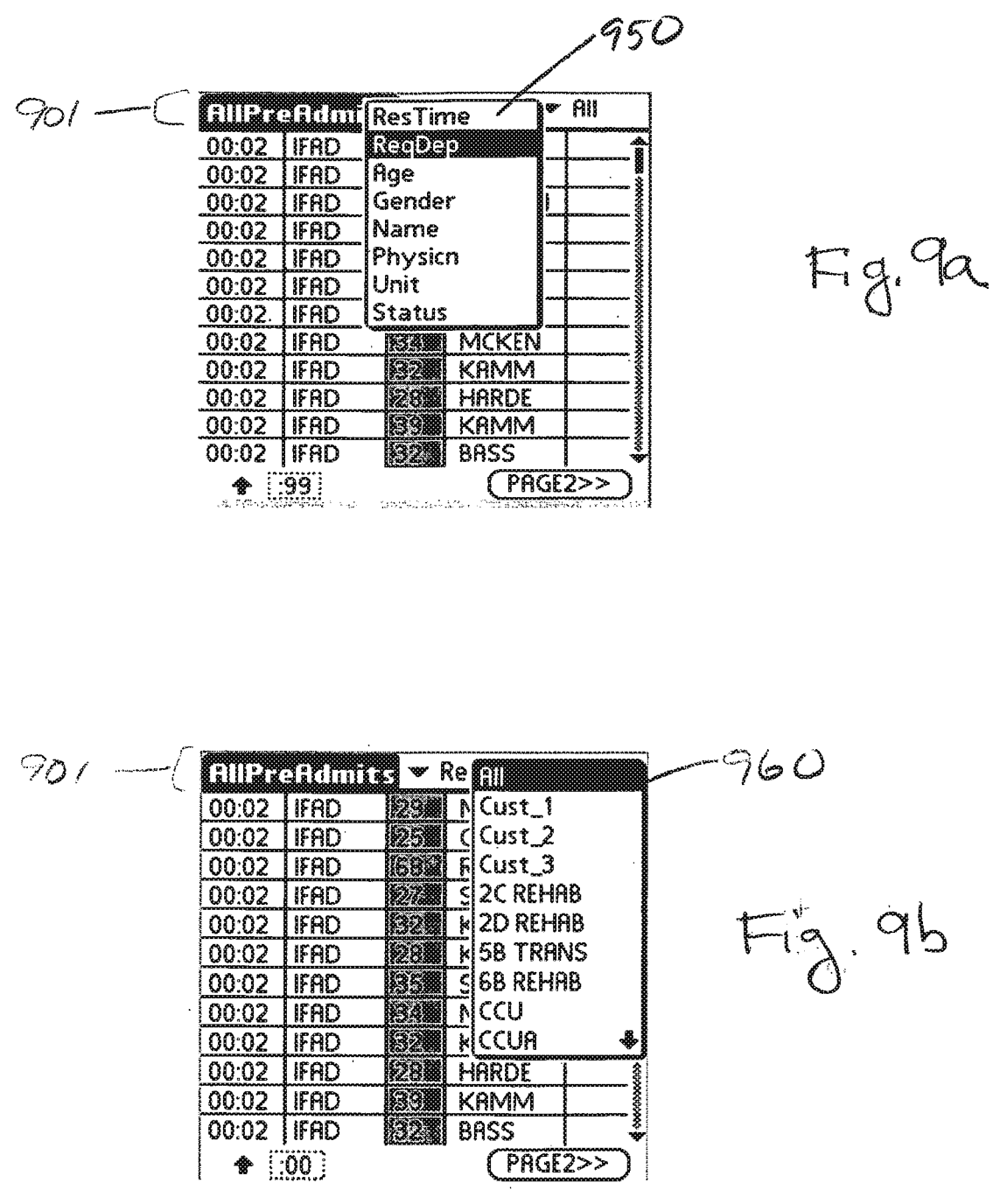

As shown in FIG. 9a, patient data presented at the All Preadmits Screen 800 can be sorted in several user-selectable ways. By way of example, a user engaging the ResTime Tab 950 located in the middle of the All PreAdmits Screen Title Menu 901 will be provided a drop down menu containing various sorting selections for the user to choose from; in the present embodiment these include sorting data by: Request Time; Requesting Department; Patient Age; Patient Gender; Patient Name; Physician; Patient Unit; and Bed Status.

As shown in FIG. 9b, users can also choose to view information for one or more specific patient units. By way of example, a user can select the All Tab 960 on All PreAdmits Screen Title Menu 901 which provides the user with a drop-down menu from which the user can select a particular patient unit. In this example, the drop-down menu contains several specific patient units, as well as three customized patient unit groups from which the user can select. It should be noted, the procedure for configuring and editing customized patient units is identical in all screens. As was indicated above a full explanation having already been given will not be repeated at this time.

Another one of the important functions of the presently embodied invention is the mobile device's ability to allow a user to change an assigned bed to a requested bed. This can be simply accomplished by selecting any of the fields for the particular patient of interest from the All Preadmits Screen 800, thereby causing the display of the Assigned Edit Screen as is set forth in FIG. 10. The user can then change the assigned bed to a requested bed by selecting the Change to Request Icon 1010. A user can add their own comments via the Comments Icon 1015 displayed on the Assigned Edit Screen 1000 as well.

The next screen of particular interest in the preferred embodiment of the present invention is the Assigned Screen 1100 as shown in FIG. 11. In the present preferred embodiment, the Assigned Screen 1100 includes 9 columns displayed on two pages. A user can move between the two pages by selecting the Select Page Icon 1200 displayed in the Assigned Screen Bottom Screen Menu 1300. A matrix containing graphically displayed icons provides information to a user related to patients. To provide an example of the scope of information which is contained in the Assigned Screen 1100, the columns contained therein as shown in FIG. 11 will be discussed, but first examples of the types of icons contained within the matrix will be mentioned. The icon at reference numeral 1110 depicts a patient's name; the icon at reference numeral 1120 depicts the assignment time; the icon at reference numeral 1130 depicts a bed identification number; the icon at reference numeral 1140 depicts a bed's status; the icon at reference numeral 1150 depicts the occupied time, i.e., the time that elapses between a patient being assigned a bed and physically occupying it; the icon at reference numeral 1160 depicts the requesters department; the icon at reference numeral 1170 depicts the patient's age; the icon at reference numeral 1180 depicts the admitting physician or department; and the icon at reference numeral 1190 depicts an abbreviated version of a patient's diagnosis.

Figures 11A, 11B:
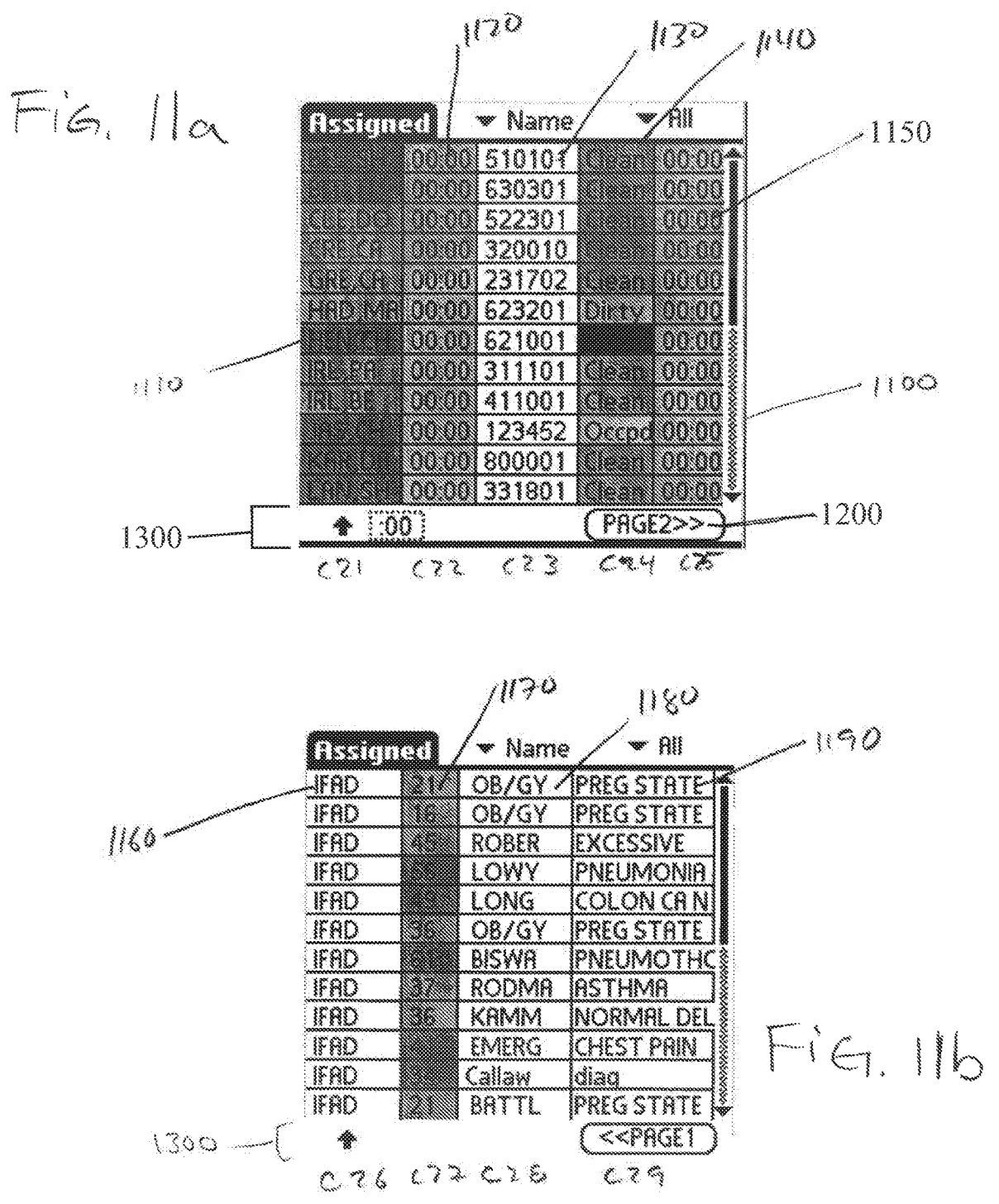

As shown in FIGS. 11a and 11b, "page 1" of the Assigned Screen 1100 contains 5 columns of information, while "page 2" of the Assigned Screen 1100 contains 4 columns of information. For purposes of illustration, these columns have been numbered, from left to right, c21-c29, respectfully. The first column, c21, contains patients' names; the second column, c22, provides information as to Assignment Time, which is the first time a request and bed assignment are received; the third column, c23, provides Identification Numbers assigned to a particular beds. The fourth column, c24, provides information as to beds' statuses, which include: clean, dirty, occupied, in progress, and blocked; the fifth column, c25, provides information on beds' occupied times, which is the time that elapsed between a patient's bed assignment and the physically occupation of the bed; the sixth column, c26, provides information as to the department making a request; the seventh column, c27, contains information as to patients' ages; the eighth column, c28, contains information of the admitting physicians or departments; the ninth column, c29, provides information of patients' abbreviated diagnoses.

From the Assigned Screen 1100 the user has a variety of useful functions that can be preformed including: sorting information options; viewing more information related to one or more patient units; and viewing more information related to user customized patient units. By way of example, as shown in FIG. 12, patient data represented at the Assigned Screen 1100 can be sorted in several user-selectable ways. A user engaging the Name Tab 1210 located in the middle of the Assigned Screen Toolbar 1220 will be provided a drop-down menu containing various sorting selections for the user to choose from; which in the present embodiment include data sorted by Requesting Department; Patient Age; Patient Gender; Patient Name; Physician; and Bed Identification Number.

Figures 12A, 12B:
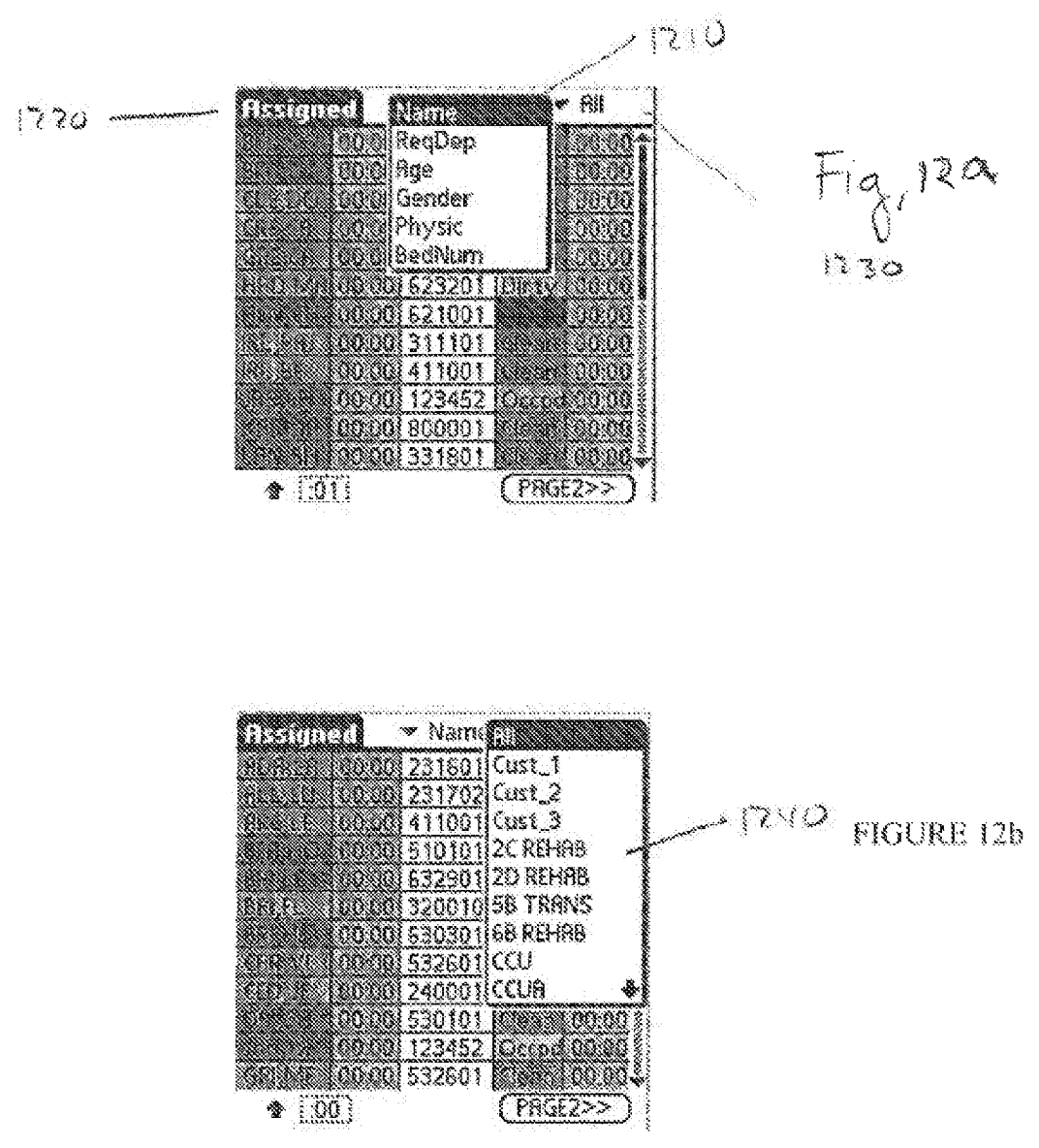

As shown in FIG. 12b, users can also choose to view information for one or more specific patient units. By way of example, a user can select the All Tab 1230 on the Assigned Screen Toolbar 1220 which provides the user with a drop-down menu 1240 from which the user can select a particular patient unit. In this example, the drop-down menu 1240 contains several specific patient units, as well as three customized patient unit groups from which the user can select.

Figures 13A, 13B, 13C:
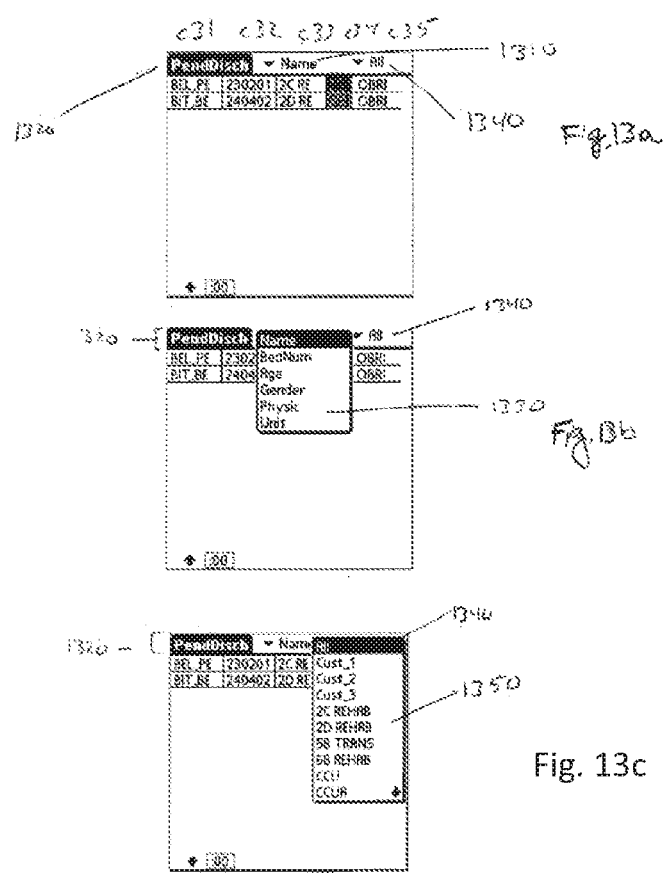
FIG. 13a illustrates a graphical depiction of a "Pending Discharges Screen" display of a mobile device in accordance with an embodiment of the present invention.
FIG. 13b illustrates a graphical depiction of a sorting options window in an "Pending Discharges Screen" display of a mobile device in accordance with an embodiment of the present invention.
FIG. 13c illustrates a graphical depiction of a dropdown Patient Units selection display of a mobile device in accordance with an embodiment of the present invention.

As shown in FIG. 13a, the Pending Discharges Screen 1300 contains 5 columns of information. For purposes of illustration, these columns have been numbered, from left to right, c31-c34, respectfully. The first column, c31, contains the patients' names; the second column, c32, provides information as to bed identification numbers; the third column, c33, provides information as to the patient units from which patients are being transferred; the fourth column, c34, provides patients' ages; and the fifth column, c35, provides information as to the admitting physicians, attending physicians or departments. From the Pending Discharges Screen 1300 the user has a variety of useful functions that can be preformed including: sorting information options; viewing more information related to one or more patient units; and viewing more information related to user customized patient units. As shown in FIG. 13b, patient data represented at the Pending Discharges Screen 1300 can be sorted in several user-selectable ways. By way of example, a user engaging the Name Tab 1310 located in the middle of the Pending Discharges Screen Toolbar 1320 will be provided a drop down menu 1330 containing various sorting selections for the user to choose from, which in the present embodiment includes data sorted by Patient Age; Patient Gender; Patient Name; Physician; Bed Identification Number; and Patient Unit.

As shown in FIG. 13c, users can also choose to view information for one or more specific patient units. By way of example, a user can select the All Tab 1340 on the Pending Discharges Screen Toolbar 1320 which provides the user with a drop-down menu 1350 from which the user can select a particular patient unit. In this example, the drop-down menu 1350 contains several specific patient units, as well as three customized patient unit groups from which the user can select.

As shown in FIG. 14a the Pending Transfers Screen 1400 contains 4 columns of information. For purposes of illustration, these columns have been numbered, from left to right, c41-c44. The first column, at c41, contains patients names; the second column, c42, provides information as to bed identification numbers; the third column, c43, provides information as to the patient units from which patients are being transferred; and the fourth column, c44, provides information as to patients' abbreviated diagnoses.

From the Pending Transfers Screen 1400 the user has a variety of useful functions that can be preformed including: sorting information options; viewing more information related to one or more patient units; and viewing more information related to user customized patient units. As shown in FIG. 14b, patient data represented at the Pending Transfers Screen 1400 can be sorted in several user-selectable ways. By way of example, a user engaging the Name Tab 1410 located in the middle of the Pending Transfers Screen Toolbar 1420 will be provided a drop down menu 1430 containing various sorting selections for the user to choose from, which in the present embodiment include data sorted by Patient Age; Patient Gender; Patient Name; Physician; Bed Identification Number; and Patient Unit.

As shown in FIG. 14c, users can also choose to view information for one or more specific patient units. By way of example, a user can select the All Tab 1440 on the Pending Transfers Screen Toolbar 1420 which provides the user with a drop-down menu 1450 from which the user can select a particular patient unit. In this example, the drop-down menu contains several specific patient units, as well as three customized patient unit groups from which the user can select.

The apparatus and method of the present embodiment also contains information of key considerations for every bed control or admitting department of a hospital related to hospital room information. By selecting the Screen Title Menu 110 of any of the mobile device's screens a drop down menu display is initiated, as shown in FIG. 15, wherein the Bedboard Screen 1510 can be selected by a user. The Bedboard Screen 1510 is displayed in the form of a matrix of information, wherein individual cells contain informational icons. In the present example, shown in FIG. 15b, the Bedboard Screen 1510 contains 6 columns of information. The first three columns and the last three columns contain the same types of information. For purposes of illustration, these columns have been numbered c51-c56. The first column, c51, contains patients' bed identification numbers; the second column, c52, provides information as to the status of patents' beds; the third column, c53, provides information as to the pre-admit statuses of patients, presently the preferred pre-admit status indicators are: assigned, pending discharge, pending transfer or confirmed discharge. Assigned indicates the bed has been reserved for a specific patient. Pending Discharge indicates the bed will be empty soon, as the patient is supposed to be going home. Pending Transfer indicates the bed will be empty soon as the patient is supposed to be placed in another bed in the hospital. Confirmed Discharge indicates the bed will be empty soon, and the patient will be leaving the hospital for sure. The forth column, c54, like the first column, c51, provides patients' bed identification numbers. In this way, the Bedboard Screen is split into two screens such that twice the information is displayed as would be the case were only the first three columns of information shown. The fifth column, c55, therefore, provides information as to the statuses of patents' beds; and the sixth column, c56, provides information as to of the pre-admit statuses of patients. The icons referenced at numeral 1520 represents a particular bed's number. The icon referenced at numeral 1530 represents a particular bed's status, which as mentioned earlier can be for example clean, dirty, occupied, in progress, and blocked. The icon referenced at numeral 1540 represents a patient's pre-admit status.

Figure 16:
FIG. 16 illustrates a graphical depiction of a "Bedboard Edit Screen" window display of a mobile device in accordance with an embodiment of the present invention.
Figure 17:
FIG. 17 illustrates a graphical depiction of a "Bed Flag" "Comments Pop-up Window" of a mobile device in accordance with an embodiment of the present invention.

By selecting any of the fields associated with a particular bed identification, a detailed view is caused to be displayed, as shown in FIG. 16. A user may modify particular fields including: projected discharge date, projected time, patient status changes, bed status, and bed flag comments. A Bed Flag Icon 1610 can be displayed allowing for personalized comments to be associated with a particular patient. For example in the present embodiment by selecting the Bed Flag Icon 1610 a Comments Pop-up Window 1700, as show in FIG. 17, is displayed allowing the user to add personalized comments to the system.

As was the case with the other mobile device screens available, a user from the Bedboard Screen 1510 has a variety of useful functions that can be preformed including: sorting information options; viewing more information related to one or more patient units; viewing more information related to user customized patient units; and viewing summarized information related to the Bedboard Screen functions. The manner in which each of these processes is accomplished will now be discussed in more detail.

Figure 18:
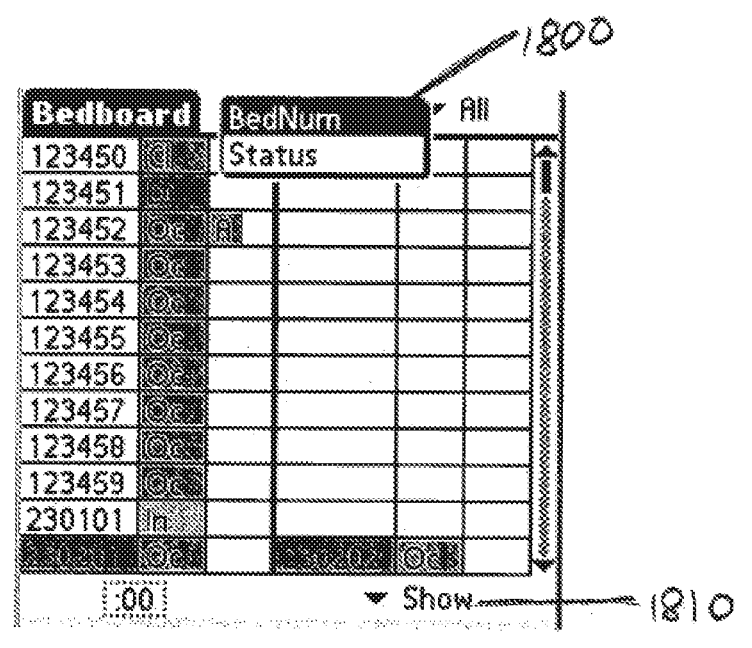

By way of example, a user engaging the Middle Tab 1550 located on the Bedboard Screen Toolbar 1560 will be provided a drop down menu 1800, as show in FIG. 18a, which contains sorting selections for the user to choose from, including bed identification numbers and the bed status information. Users can also choose whether to display one or more of the following options non-pending discharges; future discharges; and holding beds. These options are accessed via the Show Icon 1810, which initiates a pop-up window, as shown in FIG. 19, allowing the user to simply select or deselect the options desired.

Figures 19, 19A:
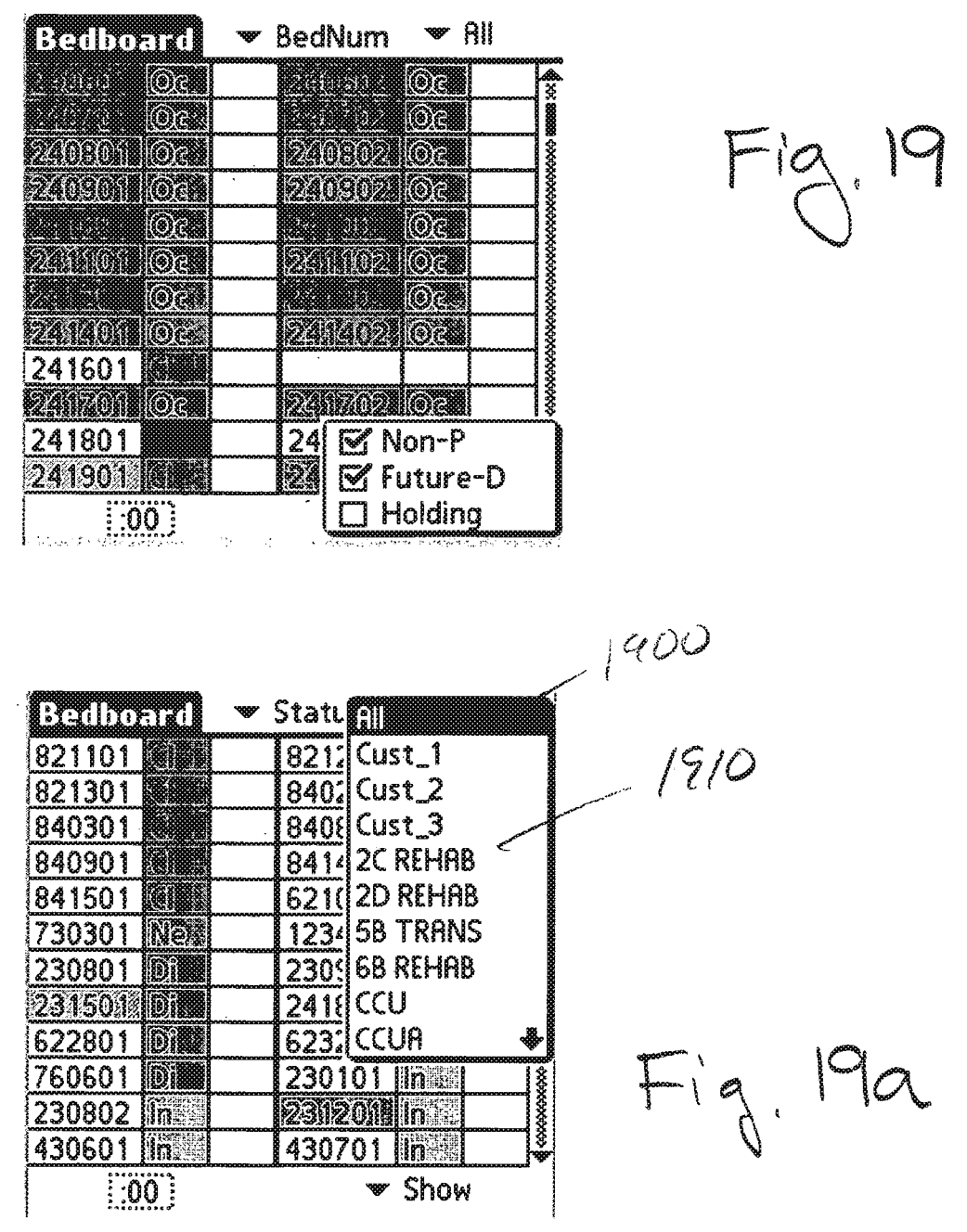

As shown in FIG. 19a, users can also choose to view information for one or more specific patient units. By way of example, a user can select the All Tab 1900 on the Bedboard Screen Toolbar, which provides the user with a drop-down menu from which the user can select a particular patient unit. In this example, the drop-down menu contains several specific patient units, as well as three customized patient unit groups from which the user can select.

As shown in FIG. 20, users can also use the device's Summary Bedboard Functions, which enables information to be displayed to the user as shown in the Summary Bedboard Screen 2000. In the preferred embodiment the information is displayed in a matrix form having at least one icon with the matrix. The Summary Bedboard Screen 2000 includes 8 columns referenced, from left to right, as c81-c88, respectfully. The information contained in the columns per the preferred embodiment include: the number of physical beds (B), the number of staffed beds (S), the number of requested beds (R), the number of assigned beds (A), the number of pending beds (P), the number of available beds (V), and Patient Census (C).

Figure 21:
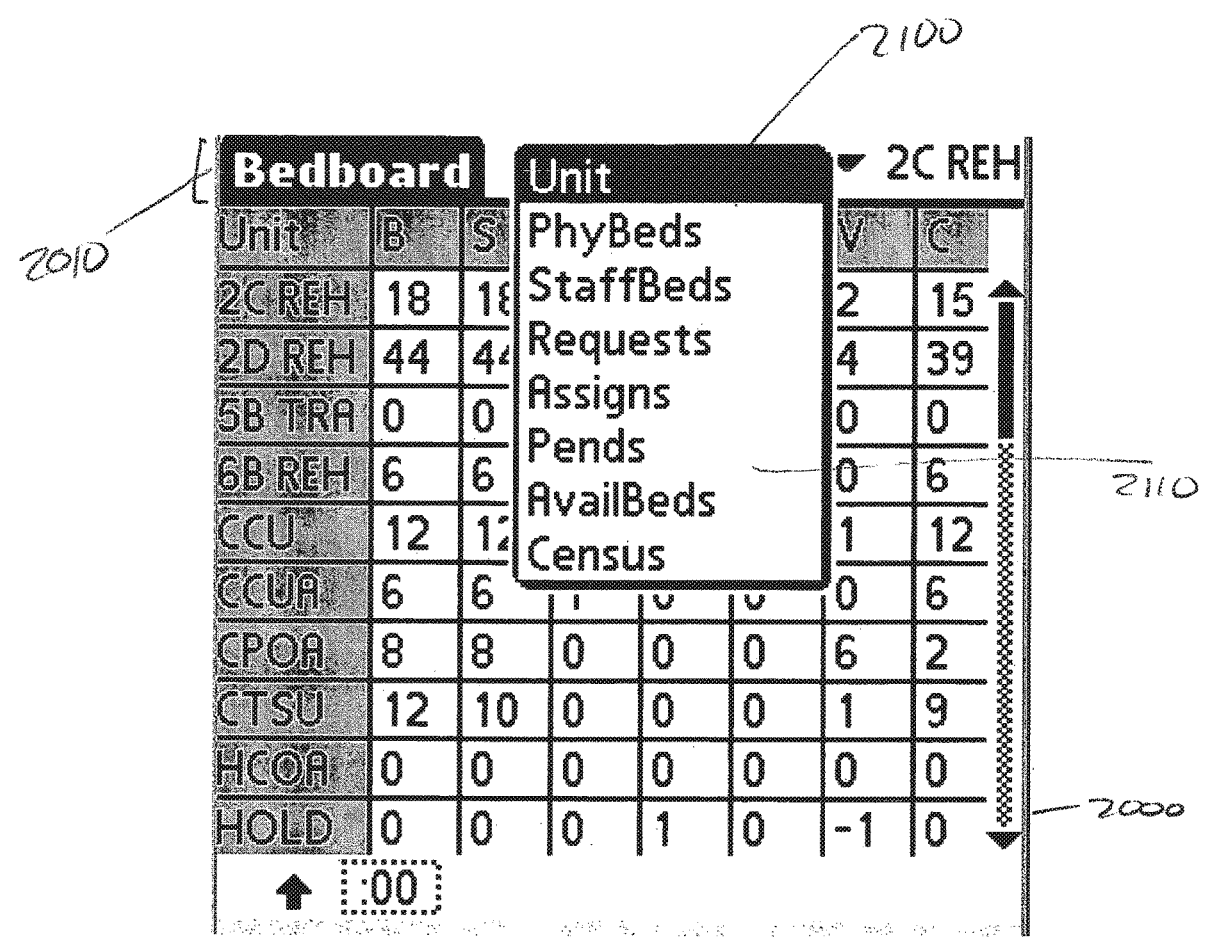

As was the case with the other screens available to the user of the mobile device, from the Summary Bedboard Screen 2000 the user has a variety of useful functions that can be preformed including: sorting information options; viewing more information related to one or more patient units; and viewing more information related to user customized patient units. By way of example, a user engaging the Middle Tab 2100 located on the Summary Bedboard Screen Toolbar 2010 will be provided a drop down menu, as show in FIG. 21, which contains sorting selections for the user to choose from, including: patient unit, physical beds, staffed beds, bed requests, assigned beds, pending transfers, available beds, and patient census.

Figure 22:
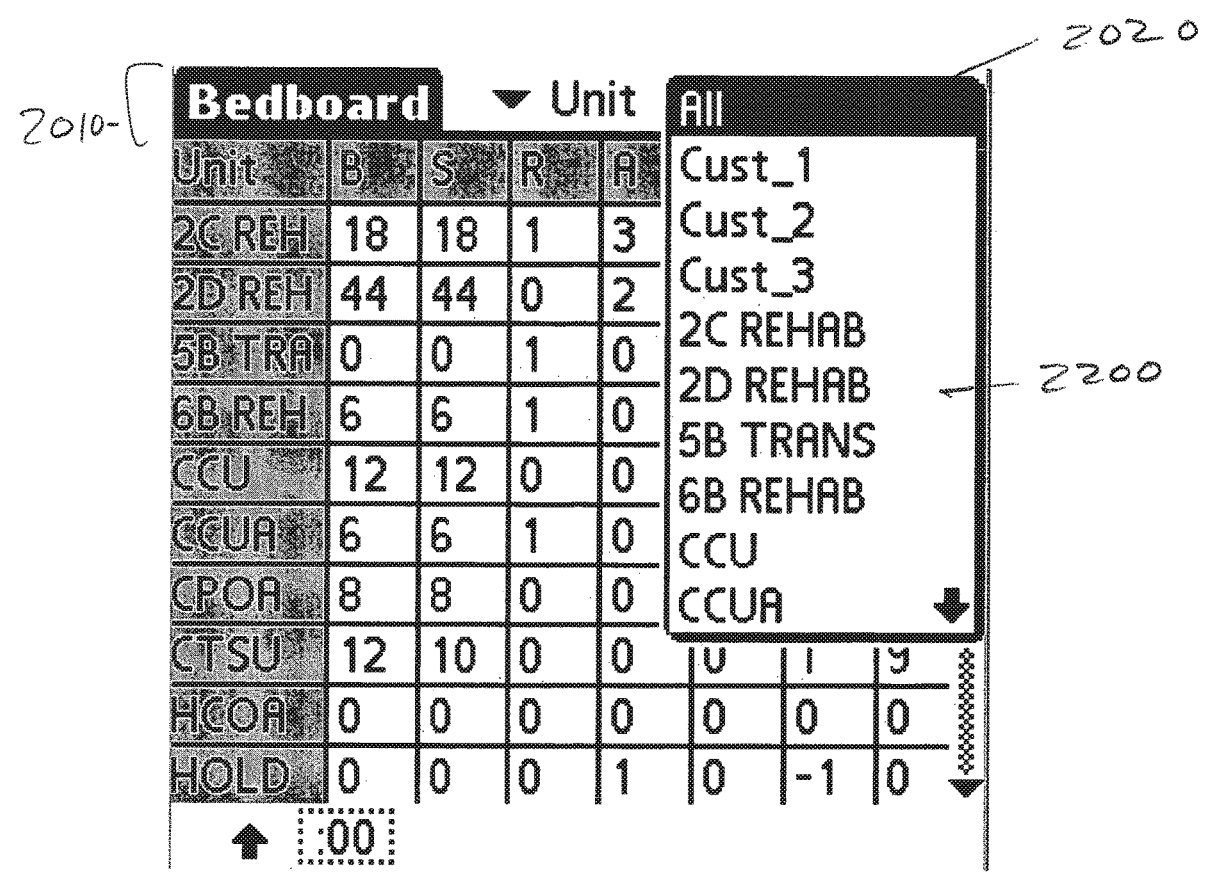

As shown in FIG. 22, users can also choose to view information for one or more specific patient units. By way of example, a user can select the All Tab 2020 on the Summary Bedboard Screen Toolbar 2010, which provides the user with a drop-down menu 2200 from which the user can select a particular patient unit. In this example, the drop-down menu contains several specific patient units, as well as three customized patient unit groups from which the user can select.

Figure 23A:
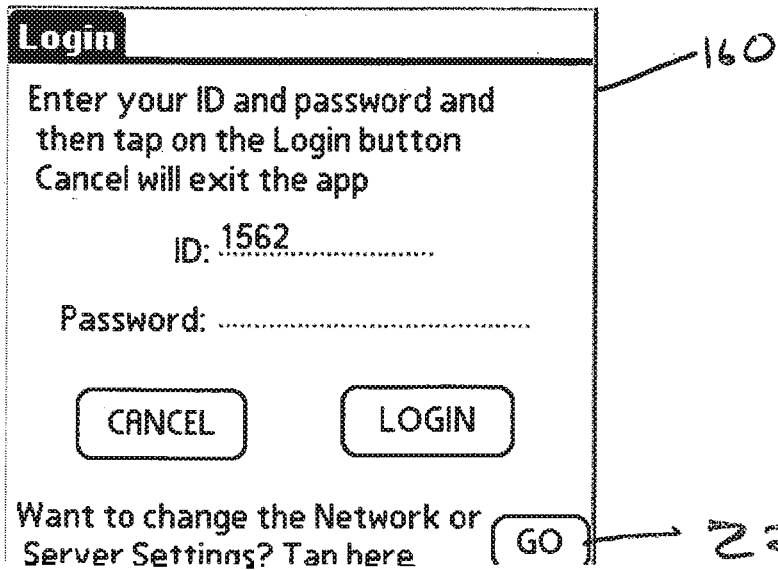
FIG. 23a illustrates a graphical depiction of a "Login Screen" display of a mobile device in accordance with an embodiment of the present invention.
Figure 23B:
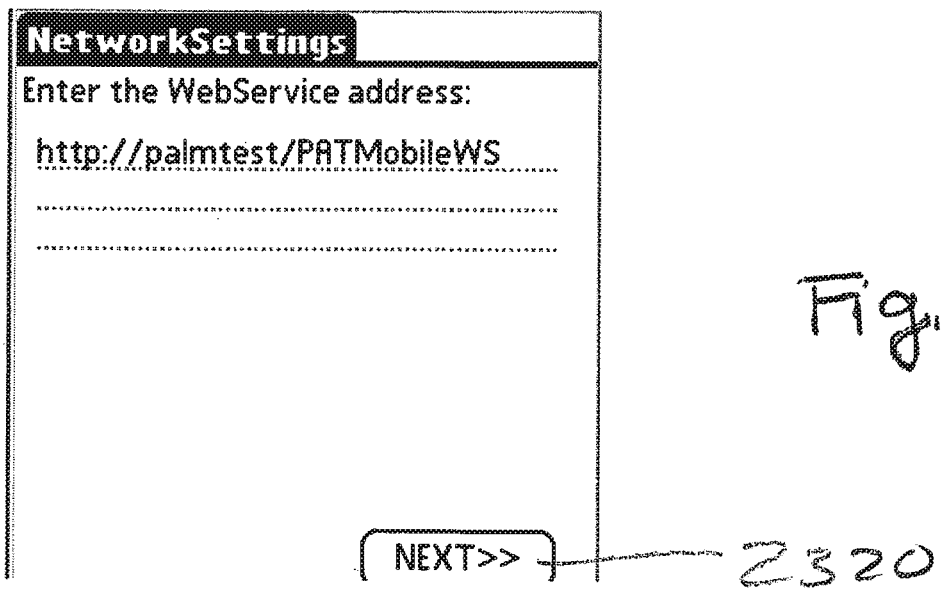
FIG. 23b illustrates a graphical depiction of a "Network Setting Screen" display of a mobile device in accordance with an embodiment of the present invention.
Figure 24A:
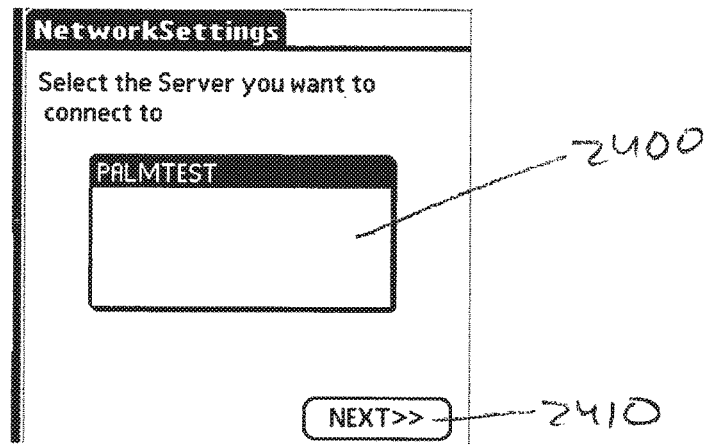
FIG. 24a illustrates a graphical depiction of a Server List Screen window display of a mobile device in accordance with an embodiment of the present invention.
Figure 24B:
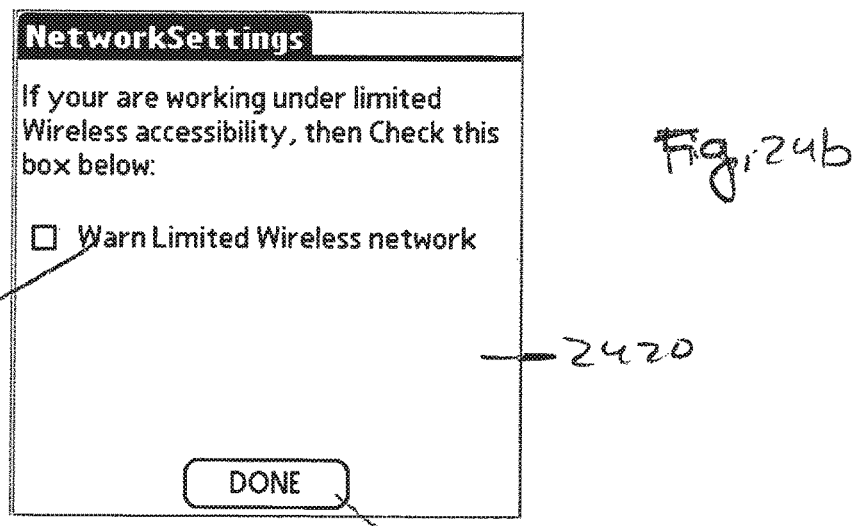
FIG. 24b illustrates a graphical depiction of a "Limited Wireless Network Screen" display of a mobile device in accordance with an embodiment of the present invention.

As indicated before, the preferred embodiment of the present invention is best performed in a wireless network environment. The process of establishing such a connection is easily performed via a Login Screen 160 as shown in FIG. 23a. By selecting the Go Icon 2310 a user will be able to enter the web service address of the wireless network provider to which the user desires to be connected. By selecting the Next Icon 2320 a Server List Screen 2400, as shown in FIG. 24a, will open and allow a user to choose from the available servers to which a connection can be established. After said selection is highlighted, a user will then select another Next Icon 2410, thereby, opening a final Limited Wireless Network Screen 2420 as shown in FIG. 24b. If the mobile device is being operated in a wireless network environment the user may finish by simply selecting the Done Icon 2430. However, if the mobile device is being used in a limited wireless network environment, the Limited Wireless Network Option 2440 can be selected by the user. By selecting the Limited Wireless Network Option 2440, the mobile device will refresh screens less frequently, but still enable the user to read the data already stored within the mobile device. The presently described preferred embodiment of the invention is also capable of operation in situations where network wireless access may become unavailable. It should be understood that in such a situation the device is capable of operation using a snapshot of both the Bedboard Screen as well a the PreAdmit Screen; therefore, the device is capable of a one time download and use.

In the preferred embodiment of the invention a fully capable wireless network environment exists, as is well known in the art, in which communication is enabled among a plurality of mobile devices via at least one wireless network server. In the present invention a mobile device will intermittently connect with the network server such that both are updated to reflect the most current information, thus, prolonging the battery life of the mobile device. It should also be understood that the update (or refresh) may be initiated by a user or be automated. While an automated update may occur at pre-determined time intervals, it is presently preferred that an automated update be initiated when certain user actions occur. For example, when more than one page of data is displayed in a screen, and a user views the second screen of data, it is presently preferred that an update be initiated when the user returns to view the first page of data. Any user action may be used to initiate an update, however, it is preferred that the selected user actions be those user actions which occur frequently.

Another aspect of the presently preferred embodiment is the use of different cell color displays to provide further information to the user of the mobile device. While many possible color schemes can be used, the preferred apparatus and method use different colored matrix cells to quickly relate information to the user as follows. Patient gender is displayed by coloring the Patient Age Cells and Patient Name Cells either pink for females or blue for males. Bed Status Cells having information as to bed statuses are colored to additionally relate the current status of a bed. In the present embodiment the following cell color associations are used: clean with green; dirty with brown; occupied with orange, in progress with yellow, and blocked with black. These same cell colors are also displayed as the highlight color with which a Bed Identification Number Cell or Icon is highlighted when selected by a user. Assignment Time Cell colors are also varied to represent different total elapsed times between receiving a request and assigning a bed. It should be understood that numerous other combinations of colors could be used and are contemplated by the present invention.

In recapitulation, the present invention, in accordance with at least one presently preferred embodiment, provides a manner of using a mobile computer device for graphically displaying and modifying information in a manner to enhance comprehension of the information and allowing a mobile and decentralized management of information to be accomplished. As such, it is to be understood that the present invention, in accordance with at least one presently preferred embodiment, may be utilized in environments other than hospitals, such as hotels, dorms, or any other situation where information about rooms and persons is desired to be graphically displayed and modified.

It is to be understood that the present invention, in accordance with at least one presently preferred embodiment, includes a display and an arrangement for producing an icon for being viewed on the display, the icon conveying information, said information consisting of bed management and patient placement information. These may be implemented on at least one general-purpose computer running suitable software programs. These may also be implemented on at least one Integrated Circuit or part of at least one Integrated Circuit. Thus, it is to be understood that the invention may be implemented in hardware, software, or a combination of both.

If not otherwise stated herein, it is to be assumed that all patents, patent applications, patent publications and other publications mentioned and cited herein are hereby fully incorporated by reference herein as if set forth in their entirety herein.

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. An apparatus for modifying and graphically displaying bed management and patient placement information, the apparatus comprising:
    a display;
    a data input/output device operatively coupled to the display;
    the display displaying a plurality of data cells, the plurality of data cells having a plurality of user modifiable attributes relating to hospital bed management information, including hospital bed occupancy obtained from a network connected system;
    said apparatus organizing the plurality of data cells in the display into a matrix format with a plurality of columns and a plurality of rows;
    said plurality of data cells comprising data cells being associated with at least: a number of physical beds, a number of staffed beds, a number of requested beds, and a number of assigned beds;
    said matrix format being displayed in a bedboard screen, whereby user interaction with a patient unit tab changes the hospital bed management information displayed in the plurality of data cells to correspond to a selected patient unit; and
    a controller which modifies at least one of the attributes of at least one of the cells to convey information.

2. The apparatus according to claim 1, further comprising:
    an arrangement for producing a plurality of icons for being viewed on the display, said icons conveying information.

3. The apparatus according to claim 2, wherein said information is related to bed management and patient placement information.

4. The apparatus according to claim 2, wherein:
    said icons have a plurality of modifiable attributes; and
    said controller modifies at least one of the attributes to convey updated information related to bed management and patient placement.

5. The apparatus according to claim 4, wherein said icons are adapted to display secondary information associated with each attribute of the icon.

6. The apparatus according to claim 5, wherein the secondary information is displayed solely to authorized users of the apparatus.

7. The apparatus according to claim 6, wherein said user can input comments.

8. The apparatus according to claim 1, wherein said cells are displayed in different colors to convey information related to bed management and patient placement.

9. The apparatus according to claim 1, wherein said apparatus comprises a mobile device.

10. The apparatus according to claim 9, wherein said mobile device is capable of updating said bed management and patient placement information via a wireless network connection.

11. A method of modifying and graphically displaying bed management and patient placement information, the method comprising the steps of:
    displaying a plurality of cells on a display of a data input/output device, the plurality of data cells having a plurality of modifiable attributes;
    said displaying comprising organizing the plurality of data cells in the display into a matrix format with a plurality of columns and a plurality of rows;
    said plurality of data cells comprising data cells being associated with at least: a number of physical beds, a number of staffed beds, a number of requested beds, and a number of assigned beds;
    said matrix format being displayed in a bedboard screen, whereby user interaction with a patient unit tab changes the hospital management information displayed in the plurality of data cells to correspond to a selected patient unit; and
    wherein at least one of the attributes of at least one of the cells is modified to convey information related to bed management and patient placement.

12. The method according to claim 11, wherein said cells are displayed in different colors to indicate information related to bed management and patient placement.

13. The method according to claim 11, further comprising the steps of:
    displaying a plurality of icons, said icons conveying information related to bed management and patient placement, said icons being positioned within said displayed cells.

14. The method according to claim 13, wherein said plurality of icons have modifiable attributes and at least one of the attributes of at least one of the icons is modified to convey information related to bed management and patient placement.

15. The method of claim 14, further comprising the steps of:
    displaying at least one patient icon within said display of information related to at least one hospital patient, each patient icon having a plurality of modifiable attributes; and
    modifying the attributes of the patient icon to convey information about the patient.

16. The method of claim 15, further comprising the steps of:
    displaying at least one bed icon within said display of information related to at least one hospital bed, each bed icon having a plurality of modifiable attributes; and
    modifying the attributes of the bed icon to convey information about the hospital bed.

17. The method of claim 15, wherein said user can input information, said input information being comments.

18. The method according to claim 13, wherein said method is implemented via a mobile device.

19. The method according to claim 18, wherein said mobile device is capable of updating said bed management and patient placement information via a wireless network connection.

20. A program storage device readable by machine, tangibly embodying a program of instructions executable by the machine to perform steps for visual presentation and user modification of information related to bed management and patient placement information, the steps comprising:
  displaying a matrix on a data input/output device;
  displaying a plurality of cells within said matrix;
  said matrix comprising a format with a plurality of columns and a plurality of rows;
  said plurality of data cells comprising data cells being associated with at least: a number of physical beds, a number of staffed beds, a number of requested beds, and a number of assigned beds;
  the plurality of data cells having user modifiable attributes relating to hospital bed management information, including hospital bed occupancy obtained from a network connected system;
  said matrix format being displayed in a bedboard screen, whereby user interaction with a patient unit tab changes the hospital bed management information displayed in the plurality of data cells to correspond to a selected patient unit; and
  modifying the attributes of said patient icon to convey information about said patient placement.

\* \* \* \* \*